US010578619B2

(12) United States Patent
Gorochov et al.

(10) Patent No.: US 10,578,619 B2
(45) Date of Patent: Mar. 3, 2020

(54) METHODS AND KITS FOR IDENTIFYING EFFECTOR TREG CELLS

(71) Applicants: INSERM (INSTITUT NATIONAL DE LA SANTE ET DE LA RECHERCHE MEDICALE), Paris (FR); UNIVERSITE PIERRE ET MARIE CURIE (PARIS 6), Paris (FR); ASSISTANCE PUBLIQUE-HOPITAUX DE PARIS (APHP), Paris (FR)

(72) Inventors: Guy Gorochov, Paris (FR); Makoto Miyara, Paris (FR)

(73) Assignees: INSERM (INSTITUT NATIONAL DE LA SANTÉ ET DE LA RECHERCHE MÉDICALE), Paris (FR); UNIVERSITÉ PIERRE ET MARIE CURIE (PARIS 6), Paris (FR); ASSISTANCE PUBLIQUE-HÔPITAUX DE PARIS (APHP), Paris (FR)

( * ) Notice: Subject to any disclaimer, the term of this patent is extended or adjusted under 35 U.S.C. 154(b) by 558 days.

(21) Appl. No.: 14/908,633

(22) PCT Filed: Jul. 30, 2014

(86) PCT No.: PCT/EP2014/066332
§ 371 (c)(1),
(2) Date: Jan. 29, 2016

(87) PCT Pub. No.: WO2015/014871
PCT Pub. Date: Feb. 5, 2015

(65) Prior Publication Data
US 2016/0169891 A1    Jun. 16, 2016

(30) Foreign Application Priority Data
Jul. 31, 2013 (EP) .................................. 13306106

(51) Int. Cl.
*G01N 33/564* (2006.01)
*G01N 33/569* (2006.01)

(52) U.S. Cl.
CPC ................ *G01N 33/56972* (2013.01); *G01N 2333/4703* (2013.01); *G01N 2333/70514* (2013.01);
(Continued)

(58) Field of Classification Search
CPC .......... G01N 33/56972; G01N 33/564; G01N 33/57484; G01N 33/6854;
(Continued)

(56) References Cited

FOREIGN PATENT DOCUMENTS

| WO | 2008/103905 A2 | 8/2008 |
| WO | 2009/047003 A1 | 4/2009 |
| WO | 2013/006474 A2 | 1/2013 |

OTHER PUBLICATIONS

Liu et al. CD127 expression inversely correlates with FoxP3 and suppressive function of human CD4+ T reg cells. JEM 203 (7): 1701-1711 (Jul. 10, 2006)—IDS.*

(Continued)

*Primary Examiner* — Gailene Gabel
(74) *Attorney, Agent, or Firm* — W&C IP

(57) ABSTRACT

The present invention relates to methods and kits for identifying effector regulatory T cells. In particular the present invention relates to use of CD15s as a biomarker for eTreg cells. The present invention also relates to a method for identifying effector Treg cells (eTreg) in a fluid sample comprising the steps of i) detecting the cell surface expression of CD4, CD25, CD127 and CD15s markers on the cell population contained in the fluid sample and ii) concluding that the cells expressing CD4, CD25, CD127 at low levels and CD15s are the effector Treg cells. The present invention also relates to a method for identifying effector Treg cells (Continued)

FoxP3 →

(eTreg) in a tissue sample comprising the steps of i) detecting the cell expression of CD4, CD25, Foxp3 and CD15s markers and ii) concluding that the cells expressing CD4, CD25, Foxp3 and CD15s are the effector Treg cells.

8 Claims, 6 Drawing Sheets

(52) U.S. Cl.
CPC ............ *G01N 2333/70596* (2013.01); *G01N 2333/7155* (2013.01); *G01N 2800/245* (2013.01); *G01N 2800/50* (2013.01); *G01N 2800/52* (2013.01); *G01N 2800/7028* (2013.01)

(58) Field of Classification Search
CPC . G01N 2333/7155; G01N 2333/70596; G01N 2333/4703; G01N 2333/70514; G01N 2333/70589; G01N 2333/705; G01N 2800/50; G01N 2800/52; G01N 2800/245; G01N 2800/7028
See application file for complete search history.

(56) References Cited

OTHER PUBLICATIONS

Ishida et al.(Clinical Utility of Monitoring Sialyl Lewis x (CD15s) Antigen on Peripheral Lymphocytes for the Diagnosis and Treatment of Rejection after Renal Transplantation. 69 (1): 59-63 (2000)—IDS.*
Liu et al., CD127 expression inversely correlates with Foxp3 and suppressive function of human CD4+ T reg cells', The Journal of Experimental Medicine, Jul. 10, 2006, pp. 1701-1711, vol. 203, No. 7.
Ishida et al., "Clinical utility of monitoring sialyl Lewis(X) (CD15S) antigen on peripheral lymphocytes for the diagnosis and treatment of rejection after renal transplantation", Transplantation, Jan 15, 2000, pp. 59-63, vol. 69, No. 1.

* cited by examiner

METHODS AND KITS FOR IDENTIFYING EFFECTOR TREG CELLS

RELATED APPLICATION

The present application claims priority to European Patent Application No. EP 13306106.9 which was filed on Jul. 31 2013. The European patent application is incorporated herein by reference in its entirety.

FIELD OF THE INVENTION

The present invention relates to methods and kits for identifying effector regulatory T cells.

BACKGROUND OF THE INVENTION

FoxP3 transcription factor expressing regulatory T (Treg) cells are instrumental for the maintenance of self tolerance[3]. While all murine FoxP3 expressing CD4+ T cells are considered effective Treg cells, their human counterpart are heterogeneous in phenotype and function[4]. Given that it is widely accepted that any human conventional CD4+ T cell can upregulate FoxP3 upon activation in the presence of IL-2 without suppressive capacities[5-9], inventors have demonstrated that not all FoxP3 expressing CD4+ T cells in PBMCs have regulatory function. Indeed, FoxP3+CD4+ T cells can be divided in (1) naïve/resting Treg cells with a CD127lowCD25++CD45RA+FoxP3low phenotype (nTreg) and (2) effector/activated Treg with CD127lowCD25+++ CD45RA-FoxP3high phenotype (eTreg), both of which being highly suppressive in vitro, and (3) CD4+ T cells that are not suppressive with a CD127lowCD25++CD45RA-FoxP3low phenotype. Inventors could also show that naïve Treg cells bearing thymic emigrant markers were precursors of effector Treg cells[10].

The relevance of this functional delineation of FoxP3 expressing CD4+ T cells could be verified in immune mediated diseases systemic lupus erythematosus (SLE) and sarcoidosis as each subset were abnormal in PBMCs as eTreg cells were markedly increased in sarcoidosis while non Treg FoxP3low cells were highly increased in active SLE[10].

Because the aforementioned classification was made on the analysis of intracellular FoxP3 expression, inventors sought to determine specific surface markers for FoxP3 expressing cells subsets. While nTreg cells can be easily defined by the CD127lowCD25++CD45RA+FoxP3low phenotype[11-13], it is still unknown how to differentiate FoxP3low non Treg cells from FoxP3high Treg cells based on the use of surface markers.

Other groups have shown that human Treg cells could be subdivided based on the expression of ICOS[14], HLA-DR[15] or intracellular expression of Helios[16], the latter being reported as specific for natural Treg cells.

However, there remains an unmet need in the art for specific surface markers for the effector/activated Treg.

The inventors therefore sought to correlate the expression of the latter surrogate differentiating markers with the expression level of FoxP3 and other surface markers.

SUMMARY OF THE INVENTION

Here inventors show, based on the extensive study of most known surface markers, that the expression of CD15s (sialyl Lewis x) can efficiently differentiate suppressive eTreg cells from FoxP3low non Treg cells. Inventors also show that CD15s expression of FoxP3 expressing CD4+ T cells in the thymus parallels other activation markers born by eTregs in the periphery. Finally, inventors show that the use of CD15s as a specific marker for eTreg cells is relevant in canonical diseases with FoxP3 expressing subsets abnormalities.

Therefore inventors describe in the present invention for the first time a surface marker that is highly specific for eTreg cells.

Thus, the present invention relates to a method for identifying effector Treg cells (eTreg) in a fluid sample comprising detecting the cell surface expression of CD4, CD25, CD127 and CD15s markers on a cell population, wherein the cells expressing CD4, CD25, CD127 at low levels and CD15s are the effector Treg cells.

The present invention relates to a method for identifying effector Treg cells (eTreg) in a tissue sample comprising detecting the cell expression of CD4, CD25, and CD15s markers on a cell population, wherein the cells expressing CD4, CD25, and CD15s are the effector Treg cells.

The invention also relates to an isolated eTreg obtainable by the method described above.

In a final aspect, the invention relates to the use of CD15s as a biomarker for eTreg.

DETAILED DESCRIPTION OF THE INVENTION

Figure 1:
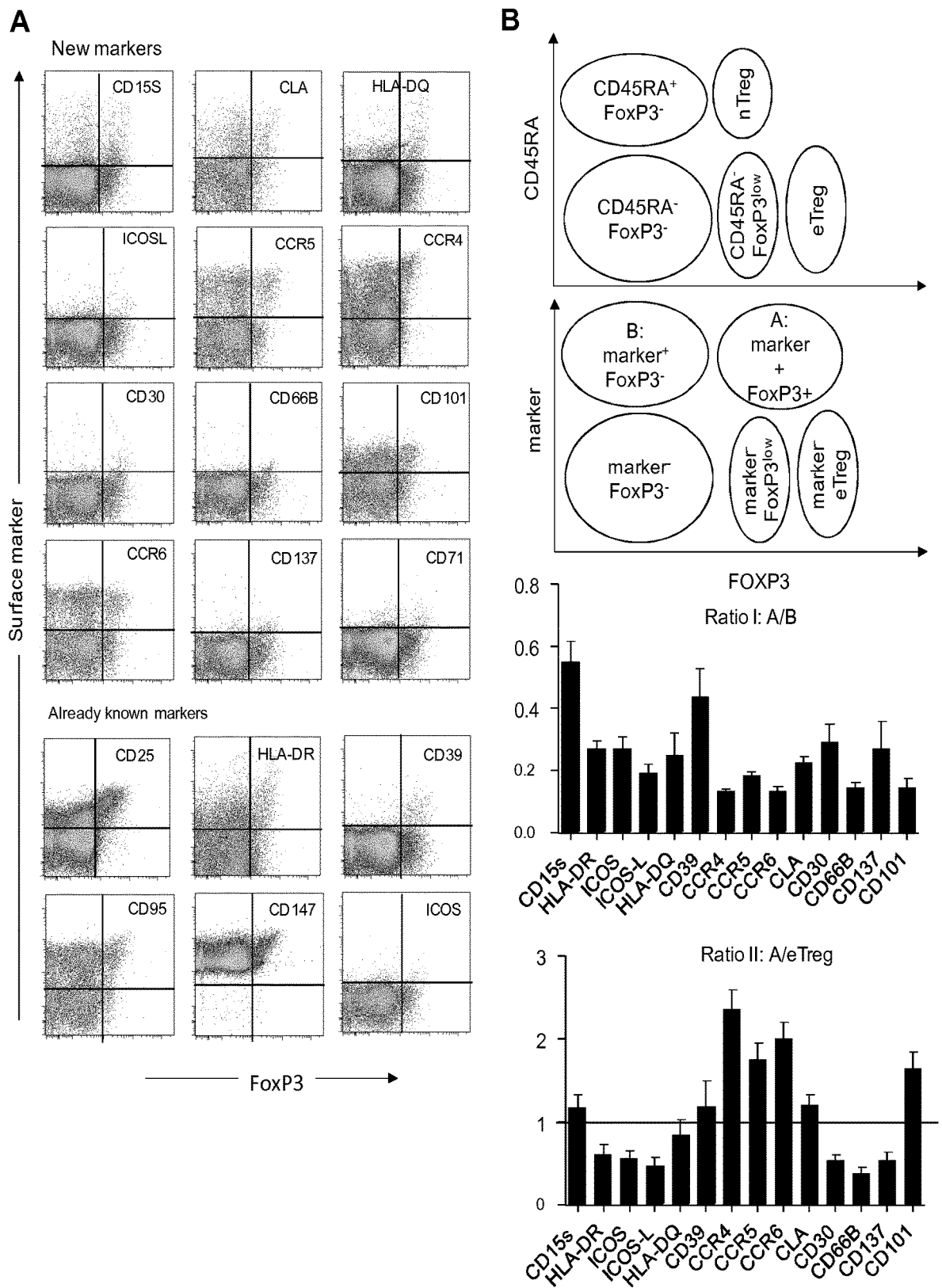
FIGS. 1 A and B. Cell surface markers for FoxP3, Helios and Ki-67 expressing CD4+ T cell subsets. (A) 18 surface markers upregulated in FoxP3$^{high}$ effector Treg cells among more than 340 analyzed. Expression of intracellular FoxP3 and each indicated surface markers by flow cytometry of PBMCs gated on CD4+ T cells. Data are representative of 6 healthy donors. (B) To assess which of the makers shown in FIG. 1A are preferentially expressed on FoxP3+CD4+ cells, we calculated the ratio of the proportion of positive cells among FoxP3+ cells (population A, shown in the lower cytometry scheme representing CD4+ T subsets defined with FoxP3 and one the aforementioned surface marker expression) to the proportion of positive cells among FoxP3− cells among CD4+ T cells (population B) for each marker (ratio I). We defined that the markers that were the most specific for FoxP3+ cells were those with the highest ratio I (upper histogram). We also verified whether such markers were preferentially expressed on eTreg cells (shown in upper cytometry scheme defined by the CD45RA−FoxP3$^{high}$ phenotype) or were also expressed on other CD45RA−FoxP3$^{low}$ non Treg cells by calculating the ratio of the proportion of CD45RA−FoxP3+ cells expressing the marker (population A, lower cytometry scheme) divided by the proportion of eTreg cells defined by the CD45RA−FoxP3$^{high}$ phenotype among CD4+ T cells (ratio II). We considered that markers with ratio II close to 1 are more specific for eTreg cells as they are not expressed by FoxP3$^{low}$ cells (lower histogram). Data are obtained from 6 healthy donors.

Method for Identifying Effector Treg Cells (eTreg)

An object of the present invention relates to a method for identifying effector Treg cells (eTreg) in a fluid sample comprising the steps of i) detecting the cell surface expression of CD4, CD25, CD127 and CD15s markers on the cell population contained in the fluid sample and ii) concluding that the cells expressing CD4, CD25, CD127 at low levels and CD15s are the effector Treg cells.

The term "T regulatory cells" (also called "Tregs" or "Treg cells") has its general meaning in the art and is intended to describe the subpopulation of T cells that are been characterised to "suppress" activity of effector T cells in vitro and/or in vivo. Treg cells thus represent an important component of the healthy immune system. Regulatory T cells are involved in keeping effector T cells in check, which modulate the immune system, maintain tolerance to self-antigens, and abrogate autoimmune and/or inflammatory disease. Tregs have numerous acknowledged biomarkers known in the art. Regulatory T cells comprise two subsets that distinguish each other by the expression of CD45RA defined as "naïve Tregs" that express FOXP3 and CD45RA and "effector Tregs" that also express FOXP3 and not CD45RA. Cells that are suitable for expansion are naïve Tregs since they are highly proliferative under stimulation conditions and in the presence of IL-2 while effector Tregs are poorly proliferative under such conditions. Thus, FoxP3+CD4+ T cells can be divided in (1) naïve/resting Treg cells with a CD127lowCD25++CD45RA+FoxP3low phenotype (naïve Treg) and (2) effector Treg with CD127lowCD25+++CD45RA-FoxP3high phenotype ("effector Treg cells"), both of which being highly suppressive in vitro, and (3) CD4+ T cells that are not suppressive with a CD127lowCD25++CD45RA-FoxP3low phenotype. Thus, the term "effector Treg cells" (also called "eTreg cells") refers to active Treg cell which display regulatory function or suppressive function of effector T cells (acting literally as the "effector" of Treg cells). The demonstration of regulatory/suppressive function of eTreg cells may be determined by any suitable method known in the art (see Miyara, M. et al. Functional Delineation and Differentiation Dynamics of Human CD4(+) T Cells Expressing the FoxP3 Transcription Factor. Immunity 30, 899-911 (2009)). In particular, examples of such tests are set out in the example section. Specifically, the tests embodied in example and FIG. 2 are regarded as standards in vitro tests for the assessment of regulatory T cell function.

In some embodiments, eTreg cells according to the present invention are mammalian eTreg cells, most particularly human eTreg cells.

The term "fluid sample" refers to any sample which is susceptible to contain a population of eTreg cells in suspension. Non-limiting examples include biological fluids such as blood (e.g., peripheral blood or umbilical cord blood), urine, lymph, cerebral spinal fluid, or ductal fluid, or such fluids diluted in a physiological solution (e.g., saline, phosphate-buffered saline (PBS), or tissue culture medium), or cells obtained from biological fluids (e.g., by centrifugation) and suspended in a physiological solution. Other examples of a "fluid sample containing cells" include cell suspensions (in physiological solutions) obtained from bone marrow aspirates, needle biopsy aspirates or biopsy specimens from, for example, lymph node or spleen.

In some embodiments, the fluid sample is a blood sample. The term "blood sample" means a whole blood sample obtained from a subject (e.g. an individual for which it is interesting to determine whether a population of eTreg cells can be identified).

In some embodiments, the fluid sample is a PBMC sample. The term "PBMC" or "peripheral blood mononuclear cells" or "unfractionated PBMC", as used herein, refers to whole PBMC, i.e. to a population of white blood cells having a round nucleus, which has not been enriched for a given sub-population. Typically, the PBMC sample may have been subjected to a selection step to contain non-adherent PBMC (which contain T cells, B cells, natural killer (NK) cells, NK T cells and DC precursors). A PBMC sample according to the invention therefore contains lymphocytes (B cells, T cells, NK cells, NKT cells). Typically, these cells can be extracted from whole blood using Ficoll, a hydrophilic polysaccharide that separates layers of blood, with the PBMC forming a cell ring under a layer of plasma. Additionally, PBMC can be extracted from whole blood using a hypotonic lysis buffer, which will preferentially lyse red blood cells. Such procedures are known to the expert in the art.

In some embodiments, the fluid sample is a sample of Treg cells in suspension. Typically, the sample of Treg cells is prepared by FACS sorting methods preformed on a PBMC sample. For example, Treg cells are isolated by using antibodies for Treg associated cell surface markers, CD4, CD25 and Foxp3. Commercial kits, e.g. CD4+CD25+Regulatory T Cell Isolation Kit from Miltenyi Biotec or Dynal® CD4+CD25+Treg Kit from Invitrogen are available. When the method is performed from a sample of Treg cells, only the detection of the cell surface expression of CD15s can be carried out. Hence, in one aspect, the invention relates to a method for identifying eTreg cells comprising the steps consisting of i) of selecting the population of CD4+/CD25+/CD127low cells ("Treg cells") from a PBMC sample and ii) identifying the population of eTreg cells by detecting the cell surface expression of CD15s.

As used herein, the term "CD4" has its general meaning in the art and refers to a cell-surface glycoprotein typically found on the mature helper T cells and immature thymocytes, as well as on monocytes and macrophages. On T cells, CD4 is the co-receptor for the T cell receptor (TCR) and recruits the tyrosine kinase lck.

As used herein, the term "CD25" refers to the alpha subunit of interleukin-2 receptor, a single-chain glycoprotein with a molecular weight of 55 kD.

As used herein, the term "CD127" refers to the interleukin-7 receptor, present on a Treg cell surface. The IL-7 receptor alpha chain is described in the literature (e.g., Goodwin et al. (1990) Cell 60:941-951).

As used herein, the term "CD15s" or "Sialyl Lewis x", also known as "sialyl CD15", or "sialyl Lex" or "Sle[x]" is a human carbohydrate adhesion molecule expressed on the cell membrane and the α2-3 sialosylated form of lacto-N-fucopentaose III (CD15). CD15s is expressed on granulocytes, monocytes and both normal and tumor cells of diverse origin. It has been shown to be a ligand for both endothelial leukocyte adhesion molecule-1 (ELAM-1 or E-selectin), and granule membrane protein-140 (GMP-140 or P-selectin). "CD15" or (lacto-N-fucopentaose III) is a cluster of differentiation antigen—an immunologically significant molecule. CD15 is a carbohydrate adhesion molecule (not a protein) that can be expressed on glycoproteins, glycolipids and proteoglycans.

Standard methods for detecting the expression of a specific surface marker such as CD15s at cell surface (e.g. Treg surface) are well known in the art. Typically, the step consisting of detecting the surface expression of a surface marker (e;g. CD15s) may consist in using at least one differential binding partner directed against the surface marker, wherein said cells are bound by said binding partners to said surface marker.

As used herein, the term "binding partner directed against the surface marker" refers to any molecule (natural or not) that is able to bind the surface marker with high affinity. The binding partners may be antibodies that may be polyclonal or monoclonal, preferably monoclonal antibodies. In another embodiment, the binding partners may be a set of aptamers.

Polyclonal antibodies of the invention or a fragment thereof can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred.

Monoclonal antibodies of the invention or a fragment thereof can be prepared and isolated using any technique that provides for the production of antibody molecules by continuous cell lines in culture. Techniques for production and isolation include but are not limited to the hybridoma technique originally; the human B-cell hybridoma technique; and the EBV-hybridoma technique.

For example, the binding partner of CD15s of the invention is the anti human CD15s antibody available from BD Pharmingen (Purified Mouse Anti-Human CD15s Clone CSLEX1) or is selected from the group consisting of the antibodies available from Santa Cruz (Clone 5F8 or clone CHO 131).

The binding partners of the invention such as antibodies or aptamers may be labelled with a detectable molecule or substance, such as preferentially a fluorescent molecule, or a radioactive molecule or any others labels known in the art. Labels are known in the art that generally provide (either directly or indirectly) a signal.

As used herein, the term "labelled", with regard to the antibody or aptamer, is intended to encompass direct labelling of the antibody or aptamer by coupling (i.e., physically linking) a detectable substance, such as a fluorophore [e.g. fluorescein isothiocyanate (FITC) or phycoerythrin (PE) or Indocyanine (Cy5)]) or a radioactive agent to the antibody or aptamer, as well as indirect labelling of the probe or antibody by reactivity with a detectable substance. An antibody or aptamer of the invention may be labelled with a radioactive molecule by any method known in the art. More particularly, the antibodies are already conjugated to a fluorophore (e.g. FITC-conjugated and/or PE-conjugated).

The aforementioned assays may involve the binding of the binding partners (ie. antibodies or aptamers) to a solid support. The solid surface could a microtitration plate coated with the binding partner for the surface marker. Alternatively, the solid surfaces may be beads, such as activated beads, magnetically responsive beads. Beads may be made of different materials, including but not limited to glass, plastic, polystyrene, and acrylic. In addition, the beads are preferably fluorescently labelled. In a preferred embodiment, fluorescent beads are those contained in TruCount™ tubes, available from Becton Dickinson Biosciences, (San Jose, Calif.). According to the invention, methods of flow cytometry are preferred methods for detecting the surface expression of the surface markers (i.e. CD4, CD25, CD127 and CD15s). Said methods are well known in the art. For example, fluorescence activated cell sorting (FACS) may be therefore used. Cell sorting protocols using fluorescent labeled antibodies directed against the surface marker (or immunobeads coated with antibody) in combination with antibodies directed against CD4, CD25 CD127, and CD15s coupled with distinct fluorochromes (or immunobeads coated with anti CD4 antibodies, anti CD25 antibodies anti CD127 antibodies and CD15s antibodies) can allow direct sorting, using cell sorters with the adequate optic configuration.

The term "low level" or "low" as used in relation to CD127' is well known in the art and refers to the expression level of the cell marker of interest (i.e. CD127), in that the expression level of the cell marker is low by comparison with the expression level of that cell marker in the population of cells being analyzed as a whole. More particularly, the term "lo" refers to a distinct population of cells that express the cell marker at a lower level than one or more other distinct population of cells. Accordingly $CD127_{low}$ refers to cells of a type that stains slightly or dully when contacted with a labeled CD127 antibody.

A further object of the present invention relates to a method for identifying effector Treg cells (eTreg) in a tissue sample comprising the steps of i) detecting the cell expression of CD4, CD25, Foxp3 and CD15s markers and ii) concluding that the cells expressing CD4, CD25, Foxp3 and CD15s are the effector Treg cells.

As used herein, the term "tissue sample" refers to a sample that is typically made up of a collection of biological cells and includes, but is not limited to, for example, biopsy samples, autopsy samples, surgical samples, cell smears, cell concentrates and cultured cells fixed on a support. Typically, the tissue sample generally includes any material for which microscopic examination of samples of the material prepared on microscope slides is desirable. The tissue sample may be collected for diagnostic, research, teaching or other purposes. The sample may be of any biological tissue. Examples of tissue samples include, but are not limited to, tissue sections of brain, adrenal glands, colon, small intestines, stomach, heart, liver, skin, kidney, lung, pancreas, testis, ovary, prostate, uterus, thyroid and spleen. The "tissue sample" as used herein may be sections of tissues that are either fresh, or frozen, or fixed and embedded. For example, tissue samples for histological examination are embedded in a support medium and moulded into standardized blocks. Paraffin wax is a known and commonly-used as a support medium, however it will be appreciated that other support media, including but not limited to, TissueTek O.C.T., manufactured by Sakura Finetek, ester, microcrystalline cellulose, bees wax, resins or polymers, such as methacrylates, may also be used as support media. Suitable resins and polymers, including Araldite 502 Kit, Eponate 12™, Kit, and Glycol Methacrylate (GMA) Kit, are available from Ted Pella, Inc., Redding, Calif.

In some embodiments, the tissue sample is a tumor sample. A "tumor sample" is a sample containing tumor material e.g. tissue material from a neoplastic lesion taken by aspiration or puncture, excision or by any other surgical method leading to biopsy or resected cellular material, including preserved material such as fresh frozen material, formalin fixed material, paraffin embedded material and the like. Such a biological sample may comprise cells obtained from a patient. The cells may be found in a cell "smear" collected, for example, by a nipple aspiration, ductal lavage, fine needle biopsy or from provoked or spontaneous nipple discharge.

As used herein, the term "Foxp3" refers to the nuclear protein Foxp3 believed to act as a transcription factor (Hori et al., 2003; Yasayko, J. E. et al., Nat. Genet 27:68-73 (2001); Fontenot, J. D. et al., Nat. Immunol. 4:330-336 (2003); Khattri, R. et al., Nat Immunol. 4:337-342 (2003)).

Typically, the detection of the markers in the tissue sample is performed with a IHC method. An immunohistochemistry (IHC) method is indeed suitable for detecting the present of eTreg cells in a tissue sample. IHC specifically provides a method of detecting targets in a tissue specimen in situ. The overall cellular integrity of the sample is maintained in IHC, thus allowing detection of both the presence and location of the targets of interest (i.e. the eTreg cells). Typically a sample is fixed with formalin, embedded in paraffin and cut into sections for staining and subsequent inspection by light microscopy. Current methods of IHC use either direct labeling or secondary antibody-based or hapten-based labeling. Examples of known IHC systems include, for example, EnVision™ (DakoCytomation), Powervision® (Immunovision, Springdale, Ariz.), the NBA™ kit (Zymed Laboratories Inc., South San Francisco, Calif.), HistoFine® (Nichirei Corp, Tokyo, Japan). In particular embodiment, a tissue section (e.g. a sample comprising eTreg cells) may be mounted on a slide or other support after incubation with antibodies directed against the CD4, CD25, FoxP3 and CD15s markers. Then, microscopic inspections in the sample mounted on a suitable solid support may be performed. For the production of photomicrographs, sections comprising samples may be mounted on a glass slide or other planar support, to highlight by selective staining the presence of the proteins of interest. Therefore IHC samples may include, for instance: (a) preparations of the tissue sample (b) fixed and embedded said cells and (c) detecting the proteins of interest in said cells samples. In some embodiments, an IHC staining procedure may comprise steps such as: cutting and trimming tissue, fixation, dehydration, paraffin infiltration, cutting in thin sections, mounting onto glass slides, baking, deparaffination, rehydration, antigen retrieval, blocking steps, applying primary antibodies, washing, applying secondary antibodies (optionally coupled to a suitable detectable label), washing, counter staining, and microscopic examination.

In some embodiments, the methods as above described further comprise a step consisting of detecting the surface expression of CD45RA wherein the cells who do not express CD45RA are eTreg cells.

As used herein the term "CD45" has its general meaning in the art and refers to the protein tyrosine phosphatase (PTP) encoded by the PTPRC gene, which is specifically expressed in hematopoietic cells. CD45 regulates receptor signalling by direct interaction with components of the receptor complexes or by activating and dephosphorylating various Src family kinases (SFK) i.e. Lck 12. But it can inhibit cytokine receptor signalling by inhibiting JAK kinases or by dephosphorylating the activating residues of Src. Typically it is possible to distinguish two isoforms of CD45: CD45RA and CD45RO.

In some embodiments, the method of the invention further comprises a step consisting of determining the level of eTreg cells present in the sample.

In some embodiments, the method of the invention further comprises a step consisting of isolating eTreg cells from the sample.

Isolated eTregs of the Invention and Uses Thereof

A further object of the invention relates to an isolated eTreg obtainable or obtained according to one of the methods described above.

As used herein, the term "isolated" refers to a cell or a population of cells which has been separated from at least some components of its natural environment.

A further object of the invention relates to an isolated substantially pure homogenous population of eTreg obtainable by one of the methods as above described.

The term "substantially pure homogenous population", as used herein, refers to a population of cells wherein the majority (e.g., at least about 80%, preferably at least about 90%, more preferably at least about 95%) of the total number of cells have the specified characteristics of the eTreg of interest.

The eTreg cells (or the substantially pure homogenous population of eTreg cells) can be used for several types of applications, which include, but are not limited to the treatment of autoimmune and/or inflammatory disease, allergic diseases and graft rejection. The eTreg cells of the invention, after administration by injection into the subject, will indeed carry out immunosuppression, resulting in the reduction of the abnormal immune reaction. Treg cell based therapy seems in theory readily applicable in humans in order to treat autoimmune diseases and allergy (Miyara M, et al (2009) Therapeutic approaches to allergy and autoimmunity based on FoxP3+ regulatory T-cell activation and expansion. J Allergy Clin Immunol 123: 749-755; quiz 756-747). Moreover, as shown in most if not all models Treg cells are characterized in vivo, by their capacity to prevent autoimmunity, sometimes to delay the onset of disease but rarely to cure diseases completely (Bluestone J A, et al (2007) What does the future hold for cell-based tolerogenic therapy? Nat Rev Immunol 7: 650-654; and Uhlig H H, et al. (2006) Characterization of Foxp3+CD4+CD25+ and IL-10-secreting CD4+CD25+ T cells during cure of colitis. J Immunol 177: 5852-5860)

Accordingly a further object of the invention relates to an isolated eTreg cell obtainable or obtained by one of the methods of the invention for use as medicament.

A further object of the invention relates to an isolated eTreg cell obtainable by one of the methods of the invention for use in the treatment of an autoimmune and/or inflammatory disease, allergic disease and in and graft rejection.

Therefore the invention relates to a pharmaceutical composition comprising a substantially pure homogenous population of eTreg cells of the invention and optionally a pharmaceutically acceptable carrier or excipient. In certain embodiments, a pharmaceutical composition may further comprise at least one biologically active substance or bioactive factor.

As used herein, the term "pharmaceutically acceptable carrier or excipient" refers to a carrier medium which does not interfere with the effectiveness of the biological activity of the Treg cells, and which is not excessively toxic to the host at the concentrations at which it is administered. Examples of suitable pharmaceutically acceptable carriers or excipients include, but are not limited to, water, salt solution (e.g., Ringer's solution), oils, gelatines, carbohydrates (e.g., lactose, amylase or starch), fatty acid esters, hydroxymethylcellulose, and polyvinyl pyroline. Pharmaceutical compositions may be formulated as liquids, semi-liquids (e.g., gels) or solids (e.g., matrix, lattices, scaffolds, and the like).

As used herein the term "biologically active substance" or "bioactive factor" refers to any molecule or compound whose presence in a pharmaceutical composition of the invention is beneficial to the subject receiving the composition. As will be acknowledged by one skilled in the art, biologically active substances or bioactive factors suitable for use in the practice of the present invention may be found in a wide variety of families of bioactive molecules and compounds. For example, a biologically active substance or bioactive factor useful in the context of the present invention may be selected from anti-inflammatory agents, anti-apoptotic agents, immunosuppressive or immunomodulatory agents, antioxidants, growth factors, and drugs.

In particular the eTreg cells according to the invention may be particularly suitable of inhibiting T cell proliferation in a subject in need thereof.

Thus a related aspect of the invention relates to a method for treating a subject suffering from auto-immune disease, allergic disease and graft rejection, said method comprising a step of administering to the subject an efficient amount of a substantially pure homogenous population of eTreg of the invention (or a pharmaceutical composition thereof).

As used herein, the term "subject" refers to a mammal, preferably a human being.

In the context of the invention, the term "treating" or "treatment", as used herein, refers to a method that is aimed at delaying or preventing the onset of a pathology, at reversing, alleviating, inhibiting, slowing down or stopping the progression, aggravation or deterioration of the symptoms of the pathology, at bringing about ameliorations of the symptoms of the pathology, and/or at curing the pathology.

As used herein, the term "efficient amount" refers to any amount of a substantially pure homogenous population of eTreg (or a pharmaceutical composition thereof) that is sufficient to achieve the intended purpose.

"Autoimmune and/or inflammatory diseases" in the context of the present invention, relates to diseases arising from an overactive immune response of the body against substances and tissues normally present in the body. In other words, the body actually attacks its own cells or components. The immune system mistakes some part of the body as a pathogen and attacks it. This may be restricted to certain organs (e.g. in thyroiditis) or involve a particular tissue in different places (e.g. Goodpasture's disease which may affect the basement membrane in both the lung and the kidney). The treatment of autoimmune and/or inflammatory diseases is typically with immunosuppression—medication which decreases the immune response. Example of autoimmune and/or inflammatory disease include but are not limited to sarcoidosis, Ankylosing Spondylitis, Crohns Disease (one of two types of idiopathic inflammatory bowel disease "IBD"), Dermatomyositis, Diabetes mellitus type 1, Goodpasture's syndrome, Graves' disease, Guillain-Barré syndrome (GBS), Hashimoto's disease, Hidradenitis suppurativa, Idiopathic thrombocytopenic purpura, systemic Lupus erythematosus, Mixed Connective Tissue Disease, Multiple Sclerosis Myasthenia gravis, Myositis, Narcolepsy, Pemphigus vulgaris, Pernicious anaemia, Psoriasis, Psoriatic Arthritis, Polymyositis, Primary biliary cirrhosis, Relapsing polychondritis, Rheumatoid arthritis, Systemic sclerosis, Temporal arteritis (also known as "giant cell arteritis"), Ulcerative Colitis (one of two types of idiopathic inflammatory bowel disease "IBD"), Vasculitis, Wegener's granulomatosis.

In a preferred embodiment the autoimmune disease is selected from the group consisting of systemic lupus erythematosus, multiple sclerosis, and vasculitis.

As used herein the term "allergic disease" refers to a hypersensitivity disorder of the immune system toward an allergen. An "allergen" comprises any substance that can cause an allergy, such as, but is not limited to, bee stings, penicillin, various food allergies, pollens, animal detritus (e.g., house dust mite, cat, dog and cockroach), mold, and fungal allergens. Example of allergic diseases include but are not limited to allergic rhinitis, allergic conjunctivitis, allergic bronchial asthma, atopic eczema, anaphylaxis, insect sting, drug allergies, food allergies, ocular allergic disease or multiple allergies (such as asthma, eczema and allergic rhinitis together). The allergic disease is seasonal or perennial.

A further aspect of the invention relates to a method for preventing or suppressing an immune response associated with rejection of a donor tissue, cell, graft, or organ transplant by a recipient subject comprising a step of administering to the subject an efficient amount of a substantially pure homogenous population of eTreg of the invention (or a pharmaceutical composition thereof).

Typically the subject may have been transplanted with a graft selected from the group consisting of heart, kidney, lung, liver, pancreas, pancreatic islets, brain tissue, stomach, large intestine, small intestine, cornea, skin, trachea, bone, bone marrow, muscle, or bladder. The method of the invention is indeed particularly suitable for preventing and treating Graft-related diseases. Graft-related diseases or disorders include graft versus host disease (GVDH), such as associated with bone marrow transplantation, and immune disorders resulting from or associated with rejection of organ, tissue, or cell graft transplantation (e.g., tissue or cell allografts or xenografts), including, e.g., grafts of skin, muscle, neurons, islets, organs, parenchymal cells of the liver, etc. With regard to a donor tissue, cell, graft or solid organ transplant in a recipient subject, it is believed that eTreg cells according to the invention may be effective in preventing acute rejection of such transplant in the recipient and/or for long-term maintenance therapy to prevent rejection of such transplant in the recipient (e.g., inhibiting rejection of insulin-producing islet cell transplant from a donor in the subject recipient suffering from diabetes). Thus the method of the invention is useful for preventing Host-Versus-Graft-Disease (HVGD) and Graft-Versus-Host-Disease (GVHD). The eTreg cells may be administered to the subject before and/or after transplantation (e.g., at least one day before transplantation, from one to five days after transplantation, etc.). In some embodiments, the eTreg cells may be administered to the subject on a periodic basis before and/or after transplantation.

Use of CD15s as a Biomarker for eTreg and Diagnostic Methods

Finally, inventors confirmed that CD15s was a relevant marker for eTreg cells in diseases. They observed that the prevalence of eTreg cells using the definition of Treg subsets based on the expression of FoxP3, CD45RA and Ki-67 was unmodified in healthy donors and slightly overestimated in sarcoidosis and slightly underestimated in SLE (systemic lupus erythematosus) when using CD15s as an additional marker for eTreg cells. Of note, the abnormalities observed in FoxP3 expressing CD4+ T cell subsets were still present and remarkable using this marker. Finally, inventors applied the method of the invention to the PBMCs of a subject with mild untreated mycosis fungoides and could observe a clear distinct population of CD15s+FoxP3high eTreg cells. As show in FIG. 5, the level of CD15s+ effector Treg cells is significantly decreased in active SLE when compared to healthy donors Accordingly a further object of the invention relates to the use of CD15s as a biomarker for eTreg cells. Because CD15s is upregulated on expanding eTreg cells, CD15s can also be used as a quality control marker to assess the purity of expanding natural Treg cells (nTregs) in vitro.

An additional object of the invention relates to an in vitro method for diagnosing a disease selected from the group consisting of autoimmune diseases, inflammatory diseases and allergic diseases in a subject, comprising the steps of determining in a sample obtained from the subject the level of a population of eTreg cells by performing one of the methods of the invention, ii) comparing the level determined in step i) with a reference value and iii) concluding that the subject suffers from the disease when the level determined at step i) is lower than the reference value.

The term "diagnosis" means the identification of the condition or the assessment of the severity of the disease.

The "reference value" generally refers to the value determined in a subject who is not affected with autoimmune and/or inflammatory diseases or allergic diseases or graft rejection. Typically the reference value is chosen in order to obtain the optimal sensitivity and specificity, i.e. the benefice/risk balance (clinical consequences of false positive and false negative). For example, the optimal sensitivity and specificity (and so the reference value) can be determined using a Receiver Operating Characteristic (ROC) curve based on experimental data obtained form a test cohort of subjects.

An additional object of the invention relates to an in vitro method for determining whether is at risk of having a disease selected from the group consisting of autoimmune diseases, inflammatory diseases and allergic diseases in a subject, comprising the steps of detecting a population of eTreg cells by performing one of the methods of the invention, wherein the presence of said population indicates that the subject is at risk of having the disease.

In some embodiments the absence of the whole population of eTreg cells (i.e. whatever antigen for which the eTreg cells are specific for) indicates that the subject is at risk of having the disease.

In some embodiments the absence of population of eTreg cells specific for an antigen (i.e. the antigen responsible for the disease) indicates that the subject is at risk of having the disease.

An additional object of the invention relates to an in vitro method for determining whether is at risk of graft rejection comprising the steps of detecting the presence or absence of a population of eTreg cells by performing one of the methods of the invention, wherein the absence of said population indicates that the subject is at risk of graft rejection.

An additional object of the invention relates to an in vitro method for determining whether is at risk of graft rejection comprising the steps of determining in a sample obtained from the subject the level of a population of eTreg cells by performing one of the methods of the invention, ii) comparing the level determined in step i) with a reference value and iii) concluding that the subject is at risk of graft rejection when the level determined at step i) is lower than the reference value.

An additional object of the invention relates to an in vitro method for monitoring a disease selected from the group consisting of autoimmune diseases, inflammatory diseases and allergic diseases comprising the steps of i) determining the level of a population of eTreg cells in a sample obtained from the subject at a first specific time of the disease by performing one of the methods of the invention, ii) determining the level of a population of eTreg cells in a sample obtained from the subject at a second specific time of the disease by performing one of the methods of the invention, iii) comparing the level determined at step i) with the level determined at step ii) and iv) concluding that the disease has evolved in worse manner when the level determined at step ii) is lower than the level determined at step i).

An additional object of the invention relates to an in vitro method for monitoring the treatment of a disease selected from the group consisting of autoimmune diseases, inflammatory diseases and allergic diseases comprising the steps of i) determining the level of a population of eTreg cells in a sample obtained from the subject before the treatment by performing one of the methods of the invention, ii) determining the level of a population of eTreg cells in a sample obtained from the subject after the treatment" by performing one of the methods of the invention, iii) comparing the level determined at step i) with the level determined at step ii) and iv) concluding that the treatment is efficient when the level determined at step ii) is higher than the level determined at step i).

The increase can be e.g. at least 5%, or at least 10%, or at least 20%, more preferably at least 30%.

Typically, in the embodiments as above described, the sample is a blood sample or a PBMC sample.

In contrast to inflammatory diseases, autoimmune diseases and allergic diseases, evidence from subjects suffering from cancer suggests that increased Treg cell activity may be associated with poor immune responses to tumour antigens and can contribute to immune dysfunction. Recent data indicate that Treg-mediated immune suppression is one of the crucial mechanisms of immune evasion by the tumour and the main obstacle of successful tumour immunotherapy (Zou, W. Regulatory T cells, tumour immunity and immunotherapy. Nature Rev. Immunol. 6, 295-307 (2006). In line with these arguments, high numbers of CD4+CD25+TReg cells have been found in subjects with lung, pancreatic, breast, liver and skin cancer, both in the blood and in the tumour itself (Zou, W. Regulatory T cells, tumour immunity and immunotherapy. Nature Rev. Immunol. 6, 295-307 (2006). Viguier, M. et al. Foxp3 expressing CD4+CD25high regulatory T cells are overrepresented in human metastatic melanoma lymph nodes and inhibit the function of infiltrating T cells. J. Immunol. 173, 1444-1453. Wolf, A. M. et al. Increase of regulatory T cells in the peripheral blood of cancer subjects. Clin. Cancer Res. 9, 606-612 (2003). Woo, E. Y. et al. Cutting edge: regulatory T cells from lung cancer subjects directly inhibit autologous T cell proliferation. J. Immunol. 168, 4272-4276 (2002)). Moreover, it has become evident that the interaction between tumours and their microenvironment is critical not only during oncogenesis and tumour progression but also in the context of anticancer therapies. Recent studies have shown that numerous anticancer agents, beyond their cytostatic properties, have the capacity to stimulate the innate and adaptive immune system, resulting—in some cases—in long-term protective memory T cell responses or in the inhibition of TReg cell function or survival, thereby facilitating tumour eradication (Galluzzi, L., et al. The secret ally: immunostimulation by anticancer drugs. Nature Rev. Drug Discov. 11, 215-233 (2012). Lesterhuis, W. J., et al. Cancer immunotherapy—revisited. Nature Rev. Drug Discov. 10, 591-600 (2011). Zitvogel, L. et al. The anticancer immune response: indispensable for therapeutic success? J. Clin. Invest. 118, 1991-2001 (2008).

An additional object of the invention relates to an in vitro method for predicting the survival of a patient suffering from a cancer comprising the steps of i) determining the level of a population of eTreg cells in a sample obtained from the subject by performing one of the methods of the invention, ii) comparing the level determined at step i) with a reference value and iii) concluding that the patient has a poor prognosis when the level determined at step i) is higher than the reference value.

The terms "cancer" "malignancy" and "tumors" refer to or describe the pathological condition in mammals that is typically characterized by unregulated cell growth. In particular, the cancer may be associated with a solid tumor or unregulated growth of undifferentiated bone marrow cells (i.e. lymphoma). Where hereinbefore and subsequently a tumor, a tumor disease, a carcinoma or a cancer are mentioned, metastasis in the original organ or tissue and/or in any other location are implicitly meant alternatively or in addition, whatever the location of the tumor and/or metastasis is. Typically, the cancer may be selected from the group consisting of bile duct cancer (e.g. periphilar cancer, distal bile duct cancer, intrahepatic bile duct cancer), bladder cancer, bone cancer (e.g. osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, lymphoma, multiple myeloma), brain and central nervous system cancer (e.g. meningioma, astocytoma, oligodendrogliomas, ependymoma, gliomas, medulloblastoma, ganglioglioma, Schwannoma, germinoma, craniopharyngioma), breast cancer (e.g. ductal carcinoma in situ, infiltrating ductal carcinoma, infiltrating, lobular carcinoma, lobular carcinoma in, situ, gynecomastia), Castleman disease (e.g. giant lymph node hyperplasia, angiofollicular lymph node hyperplasia), cervical cancer, colorectal cancer, endometrial cancer (e.g. endometrial adenocarcinoma, adenocanthoma, papillary serous adnocarcinroma, clear cell), esophagus cancer, gallbladder cancer (mucinous adenocarcinoma, small cell carcinoma), gastrointestinal carcinoid tumors (e.g. choriocarcinoma, chorioadenoma destruens), Hodgkin's disease, non-Hodgkin's lymphoma, Kaposi's sarcoma, kidney cancer (e.g. renal cell cancer), laryngeal and hypopharyngeal cancer, liver cancer (e.g. hemangioma, hepatic adenoma, focal nodular hyperplasia, hepatocellular carcinoma), lung cancer (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g. embryonal rhabdomyosarcoma, alveolar rhabdomyosarcoma, pleomorphic rhabdomyo sarcoma), salivary gland cancer, skin cancer (e.g. melanoma, nonmelanoma skin cancer), stomach cancer, testicular cancer (e.g. seminoma, nonseminoma germ cell cancer), thymus cancer, thyroid cancer (e.g. follicular carcinoma, anaplastic carcinoma, poorly differentiated carcinoma, medullary thyroid carcinoma, thyroid lymphoma), vaginal cancer, vulvar cancer, and uterine cancer (e.g. uterine leiomyosarcoma).

In some embodiments, the sample obtained from the subject is a tumor sample.

Reference values used for comparison may comprise "cut-off" or "threshold" values that may be determined as described herein. Each reference ("cut-off") value for each gene of interest may be predetermined by carrying out a method comprising the steps of a) providing a collection of tumor tissue samples from patients suffering from a cancer;

b) determining the level of eTreg cells for each tumour tissue sample contained in the collection provided at step a);

c) ranking the tumor tissue samples according to said expression level d) classifying said tumour tissue samples in pairs of subsets of increasing, respectively decreasing, number of members ranked according to their level of eTreg cells, e) providing, for each tumour tissue sample provided at step a), information relating to the actual clinical outcome for the corresponding cancer patient (i.e. the duration of the disease-free survival (DFS) or the overall survival (OS) or both);

f) for each pair of subsets of tumour tissue samples, obtaining a Kaplan Meier percentage of survival curve;

g) for each pair of subsets of tumour tissue samples calculating the statistical significance (p value) between both subsets h) selecting as reference value for the expression level, the value of expression level for which the p value is the smallest.

For example the level of eTregs cells has been assessed for 100 cancer samples of 100 patients. The 100 samples are ranked according to their expression level. Sample 1 has the best level of eTreg cells and sample 100 has the worst level of eTreg cells. A first grouping provides two subsets: on one side sample Nr 1 and on the other side the 99 other samples. The next grouping provides on one side samples 1 and 2 and on the other side the 98 remaining samples etc., until the last grouping: on one side samples 1 to 99 and on the other side sample Nr 100. According to the information relating to the actual clinical outcome for the corresponding cancer patient, Kaplan Meier curves are prepared for each of the 99 groups of two subsets. Also for each of the 99 groups, the p value between both subsets was calculated.

The reference value is selected such as the discrimination based on the criterion of the minimum p value is the strongest. In other terms, the level of eTreg cells corresponding to the boundary between both subsets for which the p value is minimum is considered as the reference value. It should be noted that the reference value is not necessarily the median value of level of eTreg cells.

In routine work, the reference value (cut-off value) may be used in the present method to discriminate tumour samples and therefore the corresponding patients.

Kaplan-Meier curves of percentage of survival as a function of time are commonly to measure the fraction of patients living for a certain amount of time after treatment and are well known by the man skilled in the art.

The man skilled in the art also understands that the same technique of assessment of the level of eTreg cells of a gene should of course be used for obtaining the reference value and thereafter for assessment of the level of eTreg cells of a gene of a patient subjected to the method of the invention.

Such reference values of level of eTreg cells may be determined for any gene defined above An additional object of the invention relates to an in vitro method for determining whether a patient suffering from a cancer will respond to a treatment comprising the steps of i) determining the level of a population of eTreg cells in a sample obtained from the subject by performing one of the methods of the invention, ii) comparing the level determined at step i) with a reference value and iii) concluding that the patient will significantly respond to the treatment when the level determined at step i) is lower than the reference value.

The treatment may consist of radiotherapy, chemotherapy or immunotherapy. The treatment may consist of an adjuvant therapy (i.e. treatment after chirurgical resection of the primary tumor) of a neoadjuvant therapy (i.e. treatment before chirurgical resection of the primary tumor).

The term "chemotherapeutic agent" refers to all chemical compounds that are effective in inhibiting tumor growth. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoraramide and trimethylolomelamine; acetogenins (especially bullatacin and bullatacinone); a carnptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estrarnustine, ifosfamide, mechlorethamine, mechlorethamine oxide hydrochloride, melphalan, novembichin, phenesterine, prednimus tine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin (11 and calicheamicin 211, see, e.g., Agnew Chem Intl. Ed. Engl. 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, canninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idanrbicin, marcellomycin, mitomycins, mycophenolic acid, nogalarnycin, olivomycins, peplomycin, potfiromycin, puromycin, quelamycin, rodorubicin, streptomgrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophospharnide glycoside; amino levulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pento statin; phenamet; pirarubicin; podophyllinic acid; 2-ethylhydrazide; procarbazine; PSK®; razoxane; rhizoxin; sizofiran; spirogennanium; tenuazonic acid; triaziquone; 2,2',2"-trichlorotriethylarnine; trichothecenes (especially T-2 toxin, verracurin A, roridinA and anguidine); urethan; vindesine; dacarbazine; mannomustine; mitobromtol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.].) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum;

etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included in this definition are antihormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

The term "immunotherapeutic agent" as used herein, refers to a compound, composition or treatment that indirectly or directly enhances, stimulates or augments the body's immune response against cancer cells and/or that lessens the side effects of other anticancer therapies. Immunotherapy is thus a therapy that directly or indirectly stimulates or enhances the immune system's responses to cancer cells and/or lessens the side effects that may have been caused by other anti-cancer agents. Immunotherapy is also referred to in the art as immunologic therapy, biological therapy biological response modifier therapy and biotherapy. Examples of common immunotherapeutic agents known in the art include, but are not limited to, cytokines, cancer vaccines, monoclonal antibodies and non-cytokine adjuvants. Alternatively the immunotherapeutic treatment may consist of administering the patient with an amount of immune cells (T cells, NK, cells, dendritic cells, B cells . . . ).

Immunotherapeutic agents can be non-specific, i.e. boost the immune system generally so that it becomes more effective in fighting the growth and/or spread of cancer cells, or they can be specific, i.e. targeted to the cancer cells themselves immunotherapy regimens may combine the use of non-specific and specific immunotherapeutic agents.

Non-specific immunotherapeutic agents are substances that stimulate or indirectly augment the immune system. Non-specific immunotherapeutic agents have been used alone as the main therapy for the treatment of cancer, as well as in addition to a main therapy, in which case the non-specific immunotherapeutic agent functions as an adjuvant to enhance the effectiveness of other therapies (e.g. cancer vaccines). Non-specific immunotherapeutic agents can also function in this latter context to reduce the side effects of other therapies, for example, bone marrow suppression induced by certain chemotherapeutic agents. Non-specific immunotherapeutic agents can act on key immune system cells and cause secondary responses, such as increased production of cytokines and immunoglobulins. Alternatively, the agents can themselves comprise cytokines. Non-specific immunotherapeutic agents are generally classified as cytokines or non-cytokine adjuvants.

A number of cytokines have found application in the treatment of cancer either as general non-specific immunotherapies designed to boost the immune system, or as adjuvants provided with other therapies. Suitable cytokines include, but are not limited to, interferons, interleukins and colony-stimulating factors.

Interferons (IFNs) contemplated by the present invention include the common types of IFNs, IFN-alpha (IFN-a), IFN-beta (IFN-beta) and IFN-gamma (IFN-y). IFNs can act directly on cancer cells, for example, by slowing their growth, promoting their development into cells with more normal behaviour and/or increasing their production of antigens thus making the cancer cells easier for the immune system to recognise and destroy. IFNs can also act indirectly on cancer cells, for example, by slowing down angiogenesis, boosting the immune system and/or stimulating natural killer (NK) cells, T cells and macrophages. Recombinant IFN-alpha is available commercially as Roferon (Roche Pharmaceuticals) and Intron A (Schering Corporation). The use of IFN-alpha, alone or in combination with other immunotherapeutics or with chemotherapeutics, has shown efficacy in the treatment of various cancers including melanoma (including metastatic melanoma), renal cancer (including metastatic renal cancer), breast cancer, prostate cancer, and cervical cancer (including metastatic cervical cancer).

Interleukins contemplated by the present invention include IL-2, IL-4, IL-11 and IL-12. Examples of commercially available recombinant interleukins include Proleukin® (IL-2; Chiron Corporation) and Neumega® (IL-12; Wyeth Pharmaceuticals). Zymogenetics, Inc. (Seattle, Wash.) is currently testing a recombinant form of IL-21, which is also contemplated for use in the combinations of the present invention. Interleukins, alone or in combination with other immunotherapeutics or with chemotherapeutics, have shown efficacy in the treatment of various cancers including renal cancer (including metastatic renal cancer), melanoma (including metastatic melanoma), ovarian cancer (including recurrent ovarian cancer), cervical cancer (including metastatic cervical cancer), breast cancer, colorectal cancer, lung cancer, brain cancer, and prostate cancer.

Interleukins have also shown good activity in combination with IFN-α in the treatment of various cancers (Negrier et al., Ann Oncol. 2002 13(9):1460-8; Touranietal, J Clin Oncol. 2003 21(21):398794).

Colony-stimulating factors (CSFs) contemplated by the present invention include granulocyte colony stimulating factor (G-CSF or filgrastim), granulocyte-macrophage colony stimulating factor (GM-CSF or sargramostim) and erythropoietin (epoetin alfa, darbepoietin). Treatment with one or more growth factors can help to stimulate the generation of new blood cells in patients undergoing traditional chemotherapy. Accordingly, treatment with CSFs can be helpful in decreasing the side effects associated with chemotherapy and can allow for higher doses of chemotherapeutic agents to be used. Various-recombinant colony stimulating factors are available commercially, for example, Neupogen® (G-CSF; Amgen), Neulasta (pelfilgrastim; Amgen), Leukine (GM-CSF; Berlex), Procrit (erythropoietin; Ortho Biotech), Epogen (erythropoietin; Amgen), Arnesp (erytropoietin). Colony stimulating factors have shown efficacy in the treatment of cancer, including melanoma, colorectal cancer (including metastatic colorectal cancer), and lung cancer.

Non-cytokine adjuvants suitable for use in the combinations of the present invention include, but are not limited to, Levamisole, alum hydroxide (alum), bacillus Calmette-Guerin (ACG), incomplete Freund's Adjuvant (IFA), QS-21, DETOX, Keyhole limpet hemocyanin (KLH) and dinitrophenyl (DNP). Non-cytokine adjuvants in combination with other immuno- and/or chemotherapeutics have demonstrated efficacy against various cancers including, for example, colon cancer and colorectal cancer (Levimasole); melanoma (BCG and QS-21); renal cancer and bladder cancer (BCG).

In addition to having specific or non-specific targets, immunotherapeutic agents can be active, i.e. stimulate the body's own immune response, or they can be passive, i.e. comprise immune system components that were generated external to the body.

Passive specific immunotherapy typically involves the use of one or more monoclonal antibodies that are specific for a particular antigen found on the surface of a cancer cell or that are specific for a particular cell growth factor. Monoclonal antibodies may be used in the treatment of cancer in a number of ways, for example, to enhance a subject's immune response to a specific type of cancer, to interfere with the growth of cancer cells by targeting specific cell growth factors, such as those involved in angiogenesis, or by enhancing the delivery of other anticancer agents to cancer cells when linked or conjugated to agents such as chemotherapeutic agents, radioactive particles or toxins.

Monoclonal antibodies currently used as cancer immunotherapeutic agents that are suitable for inclusion in the combinations of the present invention include, but are not limited to, rituximab (Rituxan®), trastuzumab (Herceptin®), ibritumomab tiuxetan (Zevalin®), tositumomab (Bexxar®), cetuximab (C-225, Erbitux®), bevacizumab (Avastin®), gemtuzumab ozogamicin (Mylotarg®), alemtuzumab (Campath®), and BL22. Monoclonal antibodies are used in the treatment of a wide range of cancers including breast cancer (including advanced metastatic breast cancer), colorectal cancer (including advanced and/or metastatic colorectal cancer), ovarian cancer, lung cancer, prostate cancer, cervical cancer, melanoma and brain tumours. Other examples include anti-CTLA4 antibodies (e.g. Ipilimumab), anti-PD1 antibodies, anti-PDLL antibodies, anti-TIMP3 antibodies, anti-LAG3 antibodies, anti-B7H3 antibodies, anti-B7H4 antibodies anti-TREM antibodies, anti-BTLA antibodies, or anti-B7H6 antibodies.

Monoclonal antibodies can be used alone or in combination with other immunotherapeutic agents or chemotherapeutic agents.

Active specific immunotherapy typically involves the use of cancer vaccines. Cancer vaccines have been developed that comprise whole cancer cells, parts of cancer cells or one or more antigens derived from cancer cells. Cancer vaccines, alone or in combination with one or more immuno- or chemotherapeutic agents are being investigated in the treatment of several types of cancer including melanoma, renal cancer, ovarian cancer, breast cancer, colorectal cancer, and lung cancer. Non-specific immunotherapeutics are useful in combination with cancer vaccines in order to enhance the body's immune response.

The immunotherapeutic treatment may consist of an adoptive immunotherapy as described by Nicholas P. Restifo, Mark E. Dudley and Steven A. Rosenberg "Adoptive immunotherapy for cancer: harnessing the T cell response, Nature Reviews Immunology, Volume 12, April 2012). In adoptive immunotherapy, the patient's circulating lymphocytes, or tumor infiltrated lymphocytes, are isolated in vitro, activated by lymphokines such as IL-2 or transuded with genes for tumor necrosis, and readministered (Rosenberg et al., 1988; 1989). The activated lymphocytes are most preferably be the patient's own cells that were earlier isolated from a blood or tumor sample and activated (or "expanded") in vitro. This form of immunotherapy has produced several cases of regression of melanoma and renal carcinoma.

The term "radiotherapeutic agent" as used herein, is intended to refer to any radiotherapeutic agent known to one of skill in the art to be effective to treat or ameliorate cancer, without limitation. For instance, the radiotherapeutic agent can be an agent such as those administered in brachytherapy or radionuclide therapy.

KITS OF THE INVENTION

A further object of the invention relates to kit comprising means for detecting the cell surface expression of CD4, CD25, CD127 and CD15s markers on a cell population.

In some embodiments, said means are antibodies. In another embodiment, these antibodies are labelled as above described.

Typically, the kits described above will also comprise one or more other containers, containing for example, wash reagents, and/or other reagents capable of quantitatively detecting the presence of bound antibodies. Preferably, the detection reagents include labelled (secondary) antibodies or, where the antibody raised against CD4, CD25, CD127 and CD15s is itself labelled, the compartments comprise antibody binding reagents capable of reacting with the labelled antibody. A compartmentalised kit includes any kit in which reagents are contained in separate containers, and may include small glass containers, plastic containers or strips of plastic or paper. Such containers may allow the efficient transfer of reagents from one compartment to another compartment whilst avoiding cross-contamination of the samples and reagents, and the addition of agents or solutions of each container from one compartment to another in a quantitative fashion. Such kits may also include a container which will accept the test sample, a container which contains the antibody(s) used in the assay, containers which contain wash reagents (such as phosphate buffered saline, Tris-buffers, and like), and containers which contain the detection reagent.

In some embodiments, the kit may further comprise means (e.g. antibodies) for detecting the expression of Foxp3 and/or CD45RA.

In a particular embodiment, a kit suitable for an IHC assay further comprises means (e.g. antibodies) for detecting the expression of Foxp3. Therefore, a further object of the invention relates to a kit comprising means (e.g. antibodies) for detecting the cell expression of CD4, CD25, Foxp3 and CD15s markers on a cell population.

Typically, a kit of the present invention will also include instructions for using the kit components to conduct the appropriate methods.

The invention will be further illustrated by the following figures and examples. However, these examples and figures should not be interpreted in any way as limiting the scope of the present invention.

Example

Material & Methods

Surface Marker Analysis of FoxP3, Ki-67 and Helios Expressing CD4+ T Cells and Flow Cytometry Blood samples were obtained from young healthy adult volunteers and from active sarcoidosis or SLE. Diagnosis of SLE and sarcoidosis were made according to previously described criteria[1,2]. The study was done according to the Helsinki declaration with the approval from the local human ethics committee (Comité Consultatif de Protection des Personnes dans la Recherche Biomédicale of Pitié-Salpétrière Hospital, Paris). For the analysis of thymocytes the approval by the Biomedecine agency (no PFS13-007) was obtained.

Human peripheral blood PBMC and human thymocytes were prepared by Ficoll gradient centrifugation and stained with anti-CD3, anti-CD8 anti-hCD4-PerCP-Cy5.5 or -APC, anti-hCD25-PE, anti-hCD45RA-PE-Cy7, anti-ICOS-, anti-HLA-DR (-PE from BD biosciences), anti-CD31 (-APC from e-bioscience), anti-hCD127 (-Pacific blue). Intracellular detection of FoxP3 with anti-hFoxP3 (PE or Alexa Fluor 647, clone 259D/A7, BD biosciences) and of Ki-67 antigen with Ki-67 antibody (FITC or PE from BD) was performed on fixed and permeabilized cells using Cytofix/Cytoperm (e-Bioscience). Most mAbs used for the study were derived from the Lyoplate system (BD). All mAbs for the cell surface marker screening were unconjugated and secondary stained.

Data were acquired by LSR-Fortessa or FACSCanto-II were analyzed with FloJo software.

Suppression Assay

PBMCs were isolated through Ficoll gradient separation from freshly drawn blood. CD4+ T cells were first magnetically isolated using a CD4 T cell separation kit (Miltenyi) and subsequently surface stained using a combination of flurochrome-conjugated mAbs: anti-CD4-PErCP 5.5, anti-CD25-PE, anti-CD127-Pacific blue, anti-CD45RA-PECy7 and anti-CD15s-AF647 obtained from BD bioscience. CD127+CD25−CD45RA+CD4+, naïve FoxP3$^{low}$CD45RA+, effector FoxP3$^{high}$CD45RA− Treg cells, CD127$^{low}$CD25+CD45RA− were flow isolated from PBMCs following flow isolation according to the gating strategy we validated previously using a FACSAria (BD bioscience)[10] and CD15s−FoxP3$^{low}$ CD4+ T cells and CD127$^{low}$CD25+CD127$^{low}$CD15s+ CD4+ T cells according to the gating strategy.

1×10$^4$ CFSE (1 μM Invitrogen)-labeled responder CD25−CD45RA+CD4+ T cells were cocultured with 1×10$^4$ unlabeled cells assessed for their suppressive capacity and 1×10$^5$ irradiated autologous accessory cells containing B cells and monocytes. Cells were stimulated with 0.5 μg/mL plate-bound anti-CD3 (OKT3 mAb) in 96-well round-bottom plate in RPMI medium supplemented with 10% fetal bovin serum (Bio West), 2 mM L-glutamin, 1 mM sodium pyruvate, 1% non essential amino acid MEM, 100 U/mL penicillin, 100 μg/ml streptomycin and amphotericin B (all from Gibco). Proliferation of CFSE-labeled cells was assessed by flow cytometry after 84-90 hr of culture.

nTreg Cells Expansion

Regarding nTreg cells expansion, 30*10^3 isolated nTreg were immediately distributed into U bottom well for culture. Cells were cultured in X-vivo 15 media, (Lonza) with 5% AB serum (Invitrogen Lifetech) and supplemented with 2 mM L-glutamin, 1 mM sodium pyruvate, 1% non essential amino acid MEM, 100 U/mL penicillin, 100 μg/ml streptomycin and amphotericin B (all from Gibco), anti-CD3/anti-CD28 coated Treg expander beads (Invitrogen Lifetech), in the presence of 300 IU/mL IL-2 (Miltenyi Biotec) in culture media alone or in the presence of Rapamycin (Sigma-Aldrich) diluted in culture medium (1 microg/mL). 300 to 1000 IU/mL IL-2 was added every 3-4 days.

Statistical Analysis

To compare the % of eTreg with CD15s+FoxP3+cells, paired t-test was performed. To compare the % of CD15s+ in healthy donors versus SLE subjects, non parametric U-Mann Whitney test was performed Results Cell Surface Markers for FoxP3, Helios and Ki-67 Expressing CD4+ T Cell Subsets To determine specific surface markers that differentiate subsets within the FoxP3 expressing CD4+ T cells, we conducted a multiparameter cytofluorometric analysis of human CD4+ T cells by analyzing CD25, CD45RA, ICOS, HLA-DR, Ki-67, Helios and FoxP3 expression together with cell surface markers.

Extensive analysis of more than 340 cell surface markers indicated that 18 surface markers were highly prevalent on eTreg cells among which 6 have been already described (CD15s, CLA, HLA-DQ, CD30, CD66B, CD101, CD275 i.e. ICOS-L, CCR5, CCR6, CCR4, CD137, CD71 and already described CD25[4], HLA-DR[15], CD39[17, 18], CD95[19], CD147[20], CD278 i.e. ICOS[14]; FIG. 1).

To assess which of those makers were preferentially expressed on FoxP3+CD4+ cells, we calculated the ratio of the proportion of positive cells among FoxP3+ cells (population A in FIG. 1b) to the proportion of positive cells among FoxP3− cells among CD4+ T cells (population B in FIG. 1b) for each marker (ratio I). We defined that the markers that were the most specific for FoxP3+ cells were those with the highest ratio I.

We also verified whether such markers were preferentially expressed on eTreg cells or were also expressed on other CD45RA−FoxP3$^{low}$ non Treg cells by calculating the ratio of the proportion of CD45RA−FoxP3+ cells expressing the marker (population A in FIG. 1b) on the proportion of eTreg cells defined by the CD45RA−FoxP3$^{high}$ phenotype among CD4+ T cells (ratio II). We considered that markers with ratio II superior to 1 were less specific for eTreg cells as they were also expressed by FoxP3$^{low}$ cells.

We observed that CD15s was the only marker with the highest ratio I. CD15s was also the only marker with a proportion of positive cells among FoxP3+ cells similar to eTreg cells proportions, i.e. ratio II close to 1 (FIG. 1b). These results indicate that CD15s is preferentially expressed on eTreg cells.

We also looked for markers that were downregulated only in eTreg cells. While 7 unknown markers were downregulated in eTregs (CD26, CD55, CD100, CD130, CD221, CD305, CD321), none of them was as discriminative as CD127[21,22].

Comparison of the expression of surface markers with the intracellular expression of proliferation marker Ki-67 and transcription factor Helios revealed that CD71 was highly correlated to the Ki-67 expression as well as ICOS and ICOS-L. This result indicates that ICOS is a good marker for proliferating eTreg cells. The only specific surface marker that corresponded to intracellular Helios expression was CD39 in some healthy donors but not all.

Because CD15s was highly expressed on FoxP3$^{high}$ eTreg cells but not on FoxP3$^{low}$CD45RA−FoxP3$^{low}$ cells and poorly expressed on FoxP3negative cells, we decided to focus our study on CD15s as a potential marker for eTreg cells.

CD15s is a Marker for Functional FoxP3$^{high}$ Treg Cells

Figure 2A:
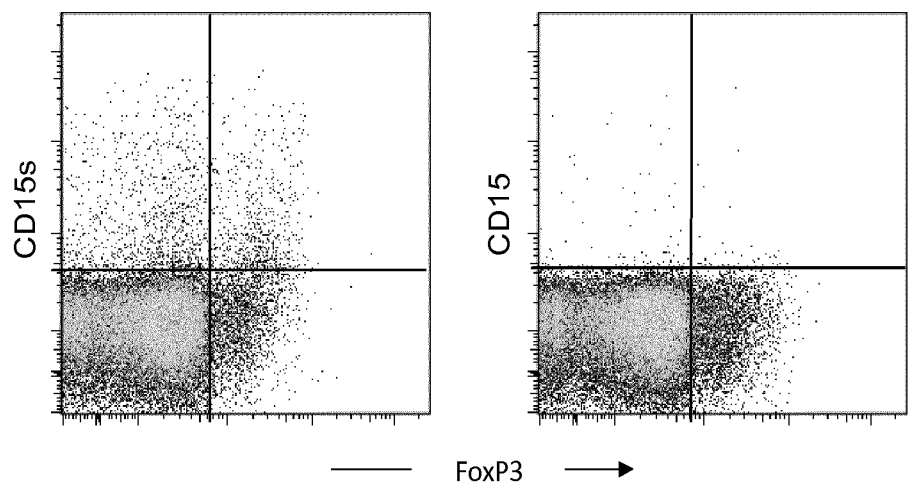
FIG. 2A-D. CD15s is a marker for functional FoxP3$^{high}$ Treg cells. (A) CD15s is expressed on eTreg cells but not non sialylated CD15. Expression of intracellular FoxP3 and indicated surface markers by flow cytometry of PBMCs gated on CD4+ T cells. Data representative of 6 independent experiments. (B) CD15s+FoxP3+ are suppressive while CD15s$^{-FoxP}$3+ cells are not. CFSE dilution by 10$^4$ labeled CD25−CD45RA+CD4+ responder T cells assessed after 84-90 hours of coculture with indicated CD4+ T cell subset at a 1 to 1 ratio with TCR stimulation. CFSE dilution by nTregs or eTregs isolated using the protocol previously described in ref 8 is used as positive controls for complete suppression. As shown by the arrows, complete suppression is characterized by fewer proliferation cycles (2 distinguishable peaks vs 4 in expanding effector cells) and decreasing amplitudes in consecutive cycle peaks while ongoing proliferation is characterized by increasing amplitudes in consecutive cycle peaks. Data are representative of 3 independent experiments. (C) Flow cytometry of the expression of CD45RA and intranuclear FoxP3(top), nuclear Ki-67 and FoxP3 (middle) and surface CD15s and intranuclear FoxP3 (bottom) in CD4$^+$ T cells. Red line separates Ki-67$^{+/-}$ FoxP3$^{high}$ from Ki-67$^-$FoxP3$^{low}$ cells and CD45RA$^{+/-}$ FoxP3$^{low}$ from CD45RA$^-$FoxP3$^{high}$ cells while black lines in bottom panels separated CD15s$^+$FoxP3$^+$ cells from CD15s$^-$FoxP3$^+$ cells. The percentages of CD45RA$^-$ FoxP3$^{high}$, Ki-67$^+$ FoxP3$^{high}$ cells and CD15s$^+$FoxP3$^{high}$ cells among CD4$^+$ cells are indicated. Data are representative of 8 independent experiments. (D) Expanding nave Treg cells upregulate CD15s in vitro. CD25$^-$CD45RA$^+$CD4$^+$ conventional T cells and nTreg cells were flow isolated and cultured for 14 days in the presence of anti-CD3/CD28 beads, IL-2 and rapamycin analyzed for CD15s and FoxP3 expression. % of CD15s$^+$ and CD15s$^-$ FoxP3$^+$ cells are indicated in corresponding quadrants. Data representative of 3 independent experiments.

We noticed that CD15S was highly expressed on eTreg cells while the non sialylated CD15 was not (FIG. 2A). CD15s is the result of the sialylation of CD15 through the fucosyltransferase 7 (alpha (1,3) fucosyltransferase). Our previous transcriptome[10] analysis of CD4+T cells expressing FoxP3 indicates that this enzyme is specifically expressed on eTreg cells subsets compared to other CD4+ T cell subsets, indicating that sialylation of CD15 is specific for eTreg cells among CD4+ T cells (Microarray data available at the National Center for Biotechnology Information Gene Expression Omnibus (GEO) accession number 15659).

Figure 2B:
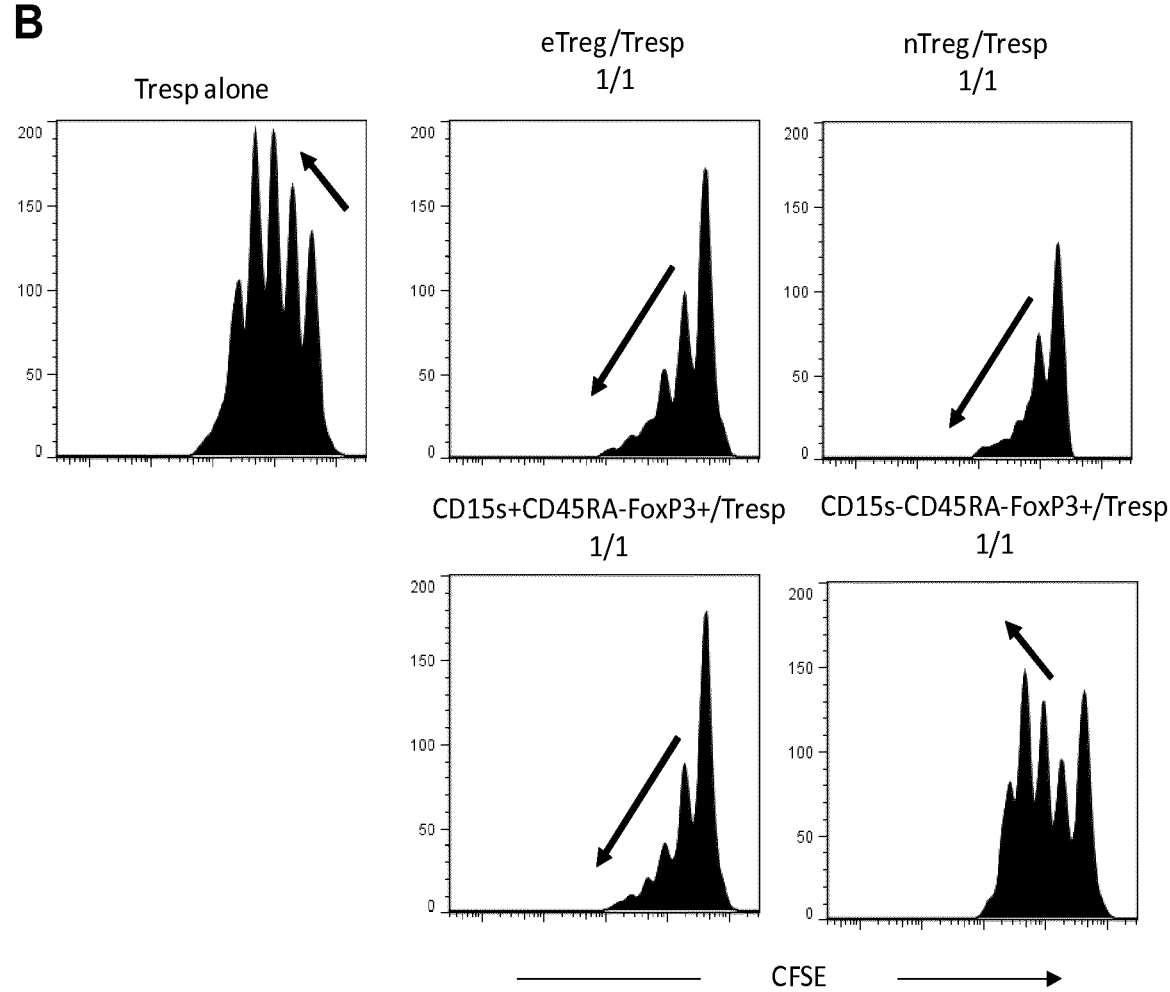

To verify that CD15s expression is indeed a marker that separates functional suppressive FoxP3 expressing CD45RA− eTreg cells from non suppressive FoxP3 expressing CD45RA− cells, we flow isolated CD15S+CD45RA−CD127$^{low}$CD25++CD4+ T cells and CD15S−CD45RA−CD127$^{low}$CD25++CD4+ T cells. As shown in FIG. 2B, CD15+FoxP3$^{high}$ cells were highly suppressive while CD15S−FoxP3$^{low}$ cells did not suppress. This indicates that CD15s is a surface marker that enables the flow separation of eTreg cells from FoxP3$^{low}$ non Treg cells in human PBMCs.

We also verified that the inflammatory cytokine profiles of CD4+ T cells subsets defined according to CD15s expression was in agreement with cytokine profiles of corresponding subsets previously defined using FoxP3 and CD45RA markers[8]. As expected, CD45RA−FoxP3+CD15s− cells were among healthy but also SLE CD4+FoxP3+ cells the highest IFN-γ and IL-2 producers.

Figures 2C, 2D:
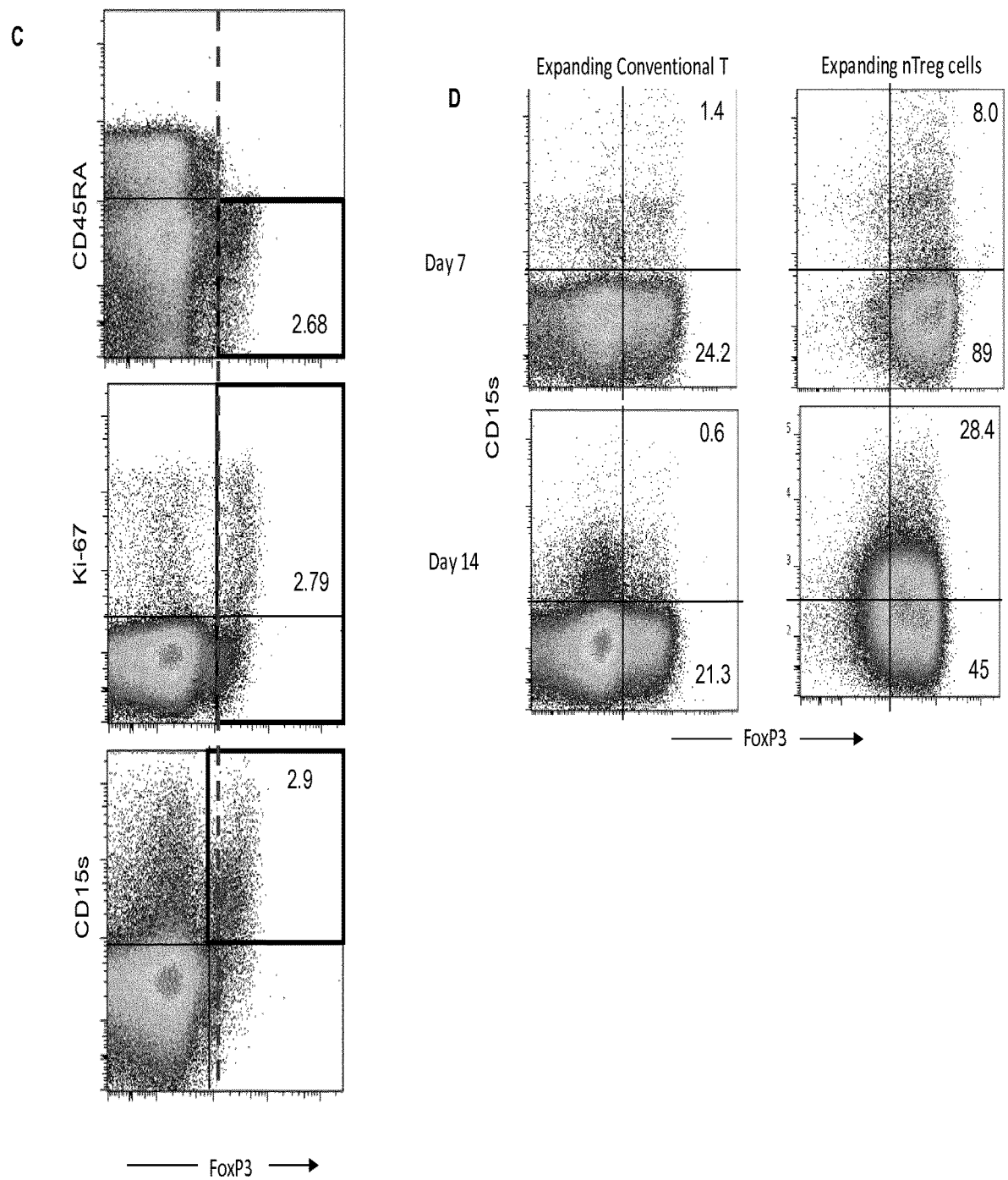

We had previously shown that the boundaries between FoxP3$^{low}$ cells (both nTreg cells and non Treg cells) and FoxP3$^{high}$ cells could be schematically defined by the vertical limit drawn by the expression of CD45RA and Ki-67 (red vertical line in FIG. 2C)[8]. As shown in FIG. 2C, the boundaries in FoxP3 expression defined by the expression of CD15s are close to the ones defined by CD45RA and Ki-67, but at slightly lower levels. The use of CD15s as a marker for FoxP3$^{high}$ cells indicates the existence of a narrow zone of overlap in FoxP3 expression between CD15s+eTreg cells and CD15s−non Treg cell (FIG. 2C).

Finally, because eTreg cells derive from nTreg cells in vivo, we also verified whether CD15s expression could be induced in expanding naïve Treg cells in vitro in the presence of high dose IL-2 and rapamycin[23,24]. While few expanding nTreg cells expressed CD15s after 7 days of culture, a significant proportion of expanding cells upregulated CD15s whereas CD15s was weakly expressed on expanding conventional CD4+ T cells (FIG. 2D). However a majority of expanding nTreg cells did not upregulate CD15s indicating that IL-2 alone and rapamycin may not be sufficient to convert all nTreg cells in efficient suppressive CD15s+ eTreg cells.

Expression of CD15s by FoxP3 Expressing Developing Treg Cells in the Thymus

Because nTreg cells that derive from the thymus do not express most markers present on eTreg cells i.e. CD25 at low levels and absence of ICOS while some developing thymic Treg cells have been reported to express these markers, we thought to determine how CD15s together with these aforementioned activation markers was expressed in the thymus by developing natural Treg cells.

As shown by others, thymic expression of FoxP3 begins at the double positive stage[25]. At this stage, developing double positive Treg cells display the FoxP3$^{high}$CD25$^{high}$ICOS+CD15s+CD45RA−CD31− phenotype and start to proliferate as some of these cells are Ki-67+. At the single CD4 positive stage, we observe two subsets of FoxP3 expressing cells, one with high expression and another with low expression of FoxP3. FoxP3$^{high}$ CD4+ thymocytes are proliferating since they express Ki-67 and share similar surface markers with proliferating double positive FoxP3$^{high}$ cells as they also express ICOS, high levels of CD25 and CD15s.

Figure 3:
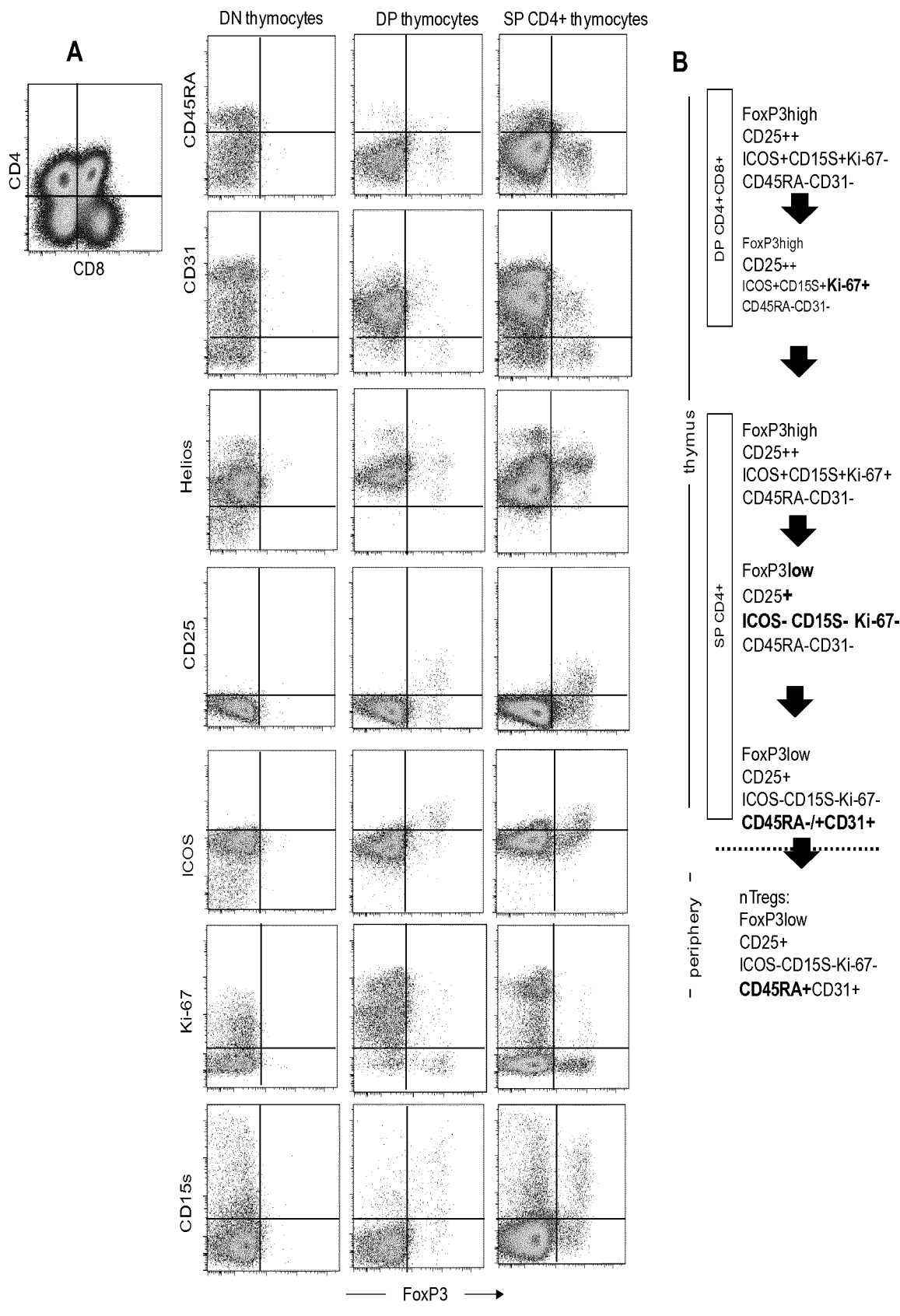
FIGS. 3A and B. Expression of CD15s by FoxP3 expressing developing Treg cells in the thymus. (A) Flow cytometry of the expression of intranuclear FoxP3 and indicated markers by double negative (DN), double positive (DP) and single positive (SP) CD4$^+$ Thymocytes. Data are representative of 3 independent experiments. (B) Modification of surface and intracellular markers by developing Treg cells in the thymus. Changes in markers are indicated in bold.

FoxP3$^{low}$ single CD4+ thymocytes can be divided in CD45RA−CD31− cells, CD45RA−CD31+ and CD45RA+ CD31+ cells that do not express either Ki-67, ICOS or, CD15s and have low levels of CD25 (FIG. 3A). We can therefore postulate that activation markers present on eTreg cells in the periphery are transiently expressed in developing Treg cells in thymus at the double positive stage and when they differentiated into single positive CD4+ T cells. Such markers are downregulated in parallel with FoxP3 expression when the FoxP3+ thymocytes acquire the naïve Treg phenotype and emigrates out of the thymus as CD45RA+ CD31+FoxP3$^{low}$CD4+ naïve Treg cells (FIG. 3B).

Thus, the analysis of human thymocytes indicates that CD15s expression parallels the expression of other Treg related markers that are transiently expressed in the thymus and absent in nTreg emigrating from the thymus.

CD15s Expression in CD4+T Cell Subsets in Canonical Diseases with FoxP3 Expressing Cell Subset Abnormalities Finally we studied the expression of CD15s in PBMCS of healthy donors (n=8) and of subjects with diseases known for the prevalence of abnormalities in FoxP3 expressing subsets i.e. sarcoidosis (n=8) and systemic lupus erythematosus (n=8).

Figure 4:
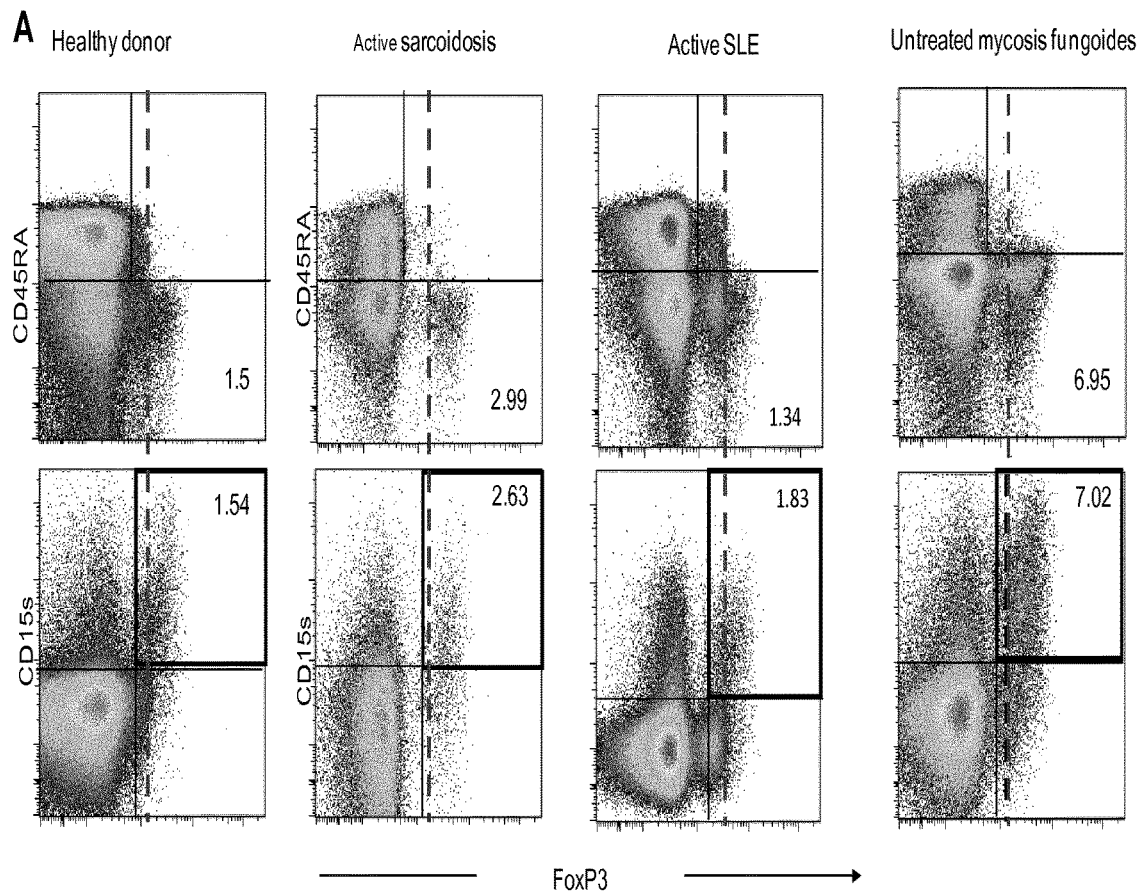
FIGS. 4A and B. CD15s expression in CD4$^+$ T cell subsets in canonical diseases with FoxP3 expressing cell subset abnormalities. (A) Flow cytometry of PBMCs gated on CD4$^+$ T cells of a representative healthy donor, a subject with active sarcoidosis and active SLE. Expression of CD45RA and FoxP3 (up) and of CD15s and FoxP3 (bottom). Numbers indicate % of eTreg cells defined by CD45RA$^-$FoxP3$^{high}$ (up) and by CD15s$^+$FoxP3$^{high}$ (bottom) phenotypes. Doted vertical line represents the threshold for FoxP3 expression for the delineation between FoxP3$^{low}$ and FoxP3$^{high}$ defined by CD45RA expression. On the right panels, the thin vertical line represents the limit between FoxP3$^{low}$ and FoxP3$^{high}$ cells defined by the expression of CD15s. (B) Comparisons of the % of eTreg cells defined by the expression of CD45RA and FoxP3 expression and by the expression of CD15s and FoxP3 in 8 healthy donors (top), 8 subjects with active sarcoidosis (middle) and 8 subjects with active SLE (bottom). Red lines and numbers represent mean %. Statistical comparisons were performed using a Student t-test. P<0.05 is considered significant. Flow cytometry of PBMCs gated on CD4$^+$ T cells of a subject with untreated mycosis fungoides analyzing the parameters described in (A).
Figure 4:
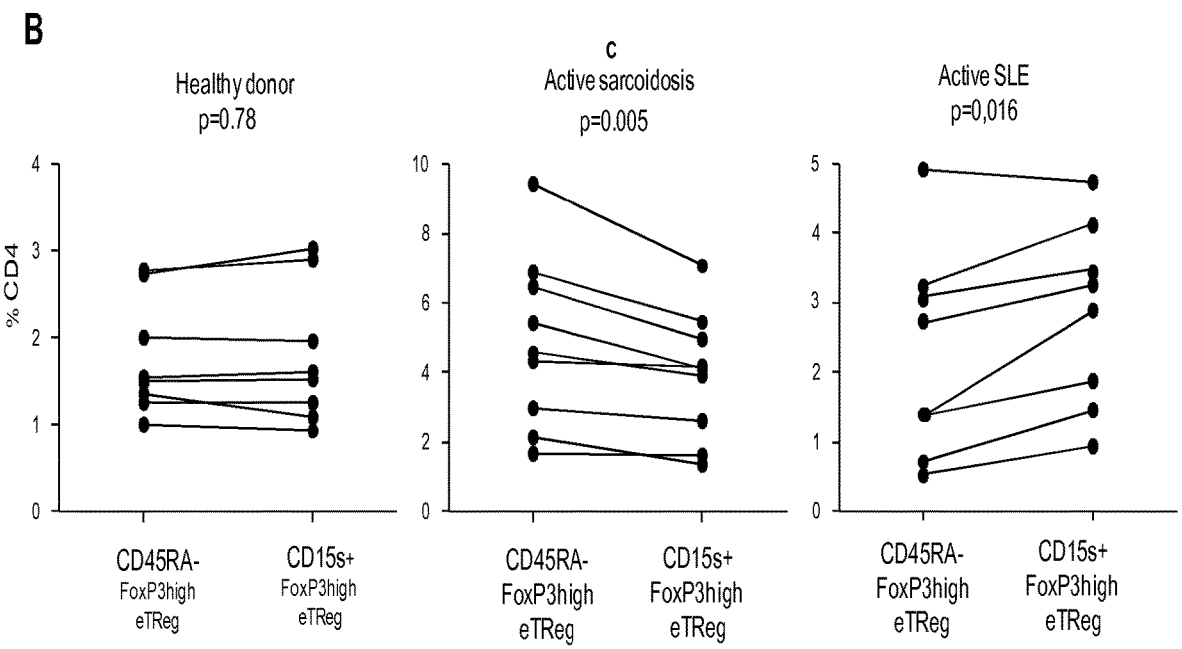
Figure 5:
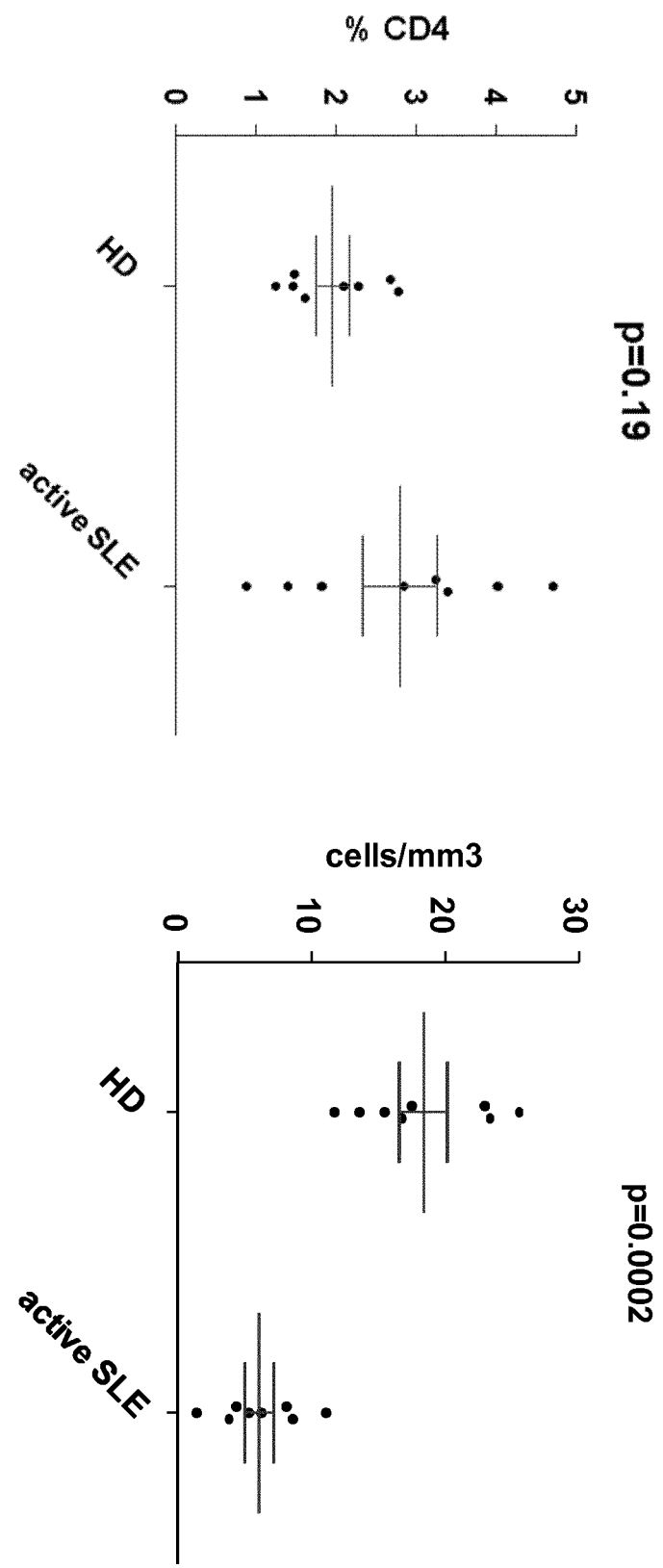
FIG. 5. The absolute count of CD15s$^+$ effector Treg cells is significantly decreased in active SLE when compared to healthy donors. Proportions among CD4$^+$T cells (A) and absolute counts (B) of CD15s$^+$effector Treg cells of the 8 healthy donors and the 8 active SLE subjects shown in FIG. 4 are compared using a non-parametric Mann-Whitney U test. Mean values with standard errors are shown in red.

In both diseases, eTreg cells could be identified using CD15s and separated from FoxP3$^{low}$ non Treg cells (FIG. 4A). Of note, we also observed, especially in SLE, that the zone of overlap in FoxP3 expression between CD15s+eTreg cells and CD15s−non Treg cells was wider. The proportion of eTreg cells measured using CD45RA and/or Ki-67 was slightly but significantly underestimated while eTreg in sarcoidosis were, yet augmented, overestimated (FIG. 4B). While the proportion of CD15s+Treg cells was not significantly different in active SLE when compared to healthy donors, the absolute counts was significantly lower, which is consistent with our previous observations[2, 10, 26] (FIGURE-5). This further indicates the necessity to add CD15s in the analysis of FoxP3 expressing CD4+ subsets in order to distinguish eTreg cells from non Treg cells efficiently especially in diseases with reported increase in FoxP3 expressing CD4+ T cells such as cancer.

We thus applied this strategy when analyzing the PBMCs of a subject with untreated mycosis fungoides which is known to display expanded circulating Treg cells[27, 28]. As shown in FIG. 4C, an increase in FoxP3 expressing CD4+ T cells with very few nTreg cells was observed. The use of CD15s as a marker for eTreg cells confirmed that eTreg cells were indeed highly increased and identifiable as a discreet population.

The combination of low expression of CD127 and high expression of CD25 in CD4+ T cells is well accepted as a surrogate to define FoxP3 expressing CD4+ T cells in humans[19, 20]. Of note, in SLE, Sjögren syndrome, systemic sclerosis, myasthenia gravis or sarcoidosis, the combination of CD127 and CD25 did not efficiently separate FoxP3+ from FoxP3− cells as a significant proportion of each FoxP3+ cells i.e. naïve Treg cells, Foxp3low CD15s− non Treg cells and CD15s+ eTreg cells resided is either CD127high or CD25− cells. This indicates that the combination of low expression of CD127 and high expression of CD25 may not be suited for the identification of FoxP3+ cell in autoimmune and/or inflammatory conditions in humans Discussion:

Because human FoxP3 expressing CD4+ T cells are heterogeneous in function[4], markers that enable their separation into suppressive Treg cells and effector T cells that express FoxP3, are required, especially in immune mediated diseases such as autoimmune and/or inflammatory/inflammatory diseases, transplantation and cancer. We had previously shown that FoxP3 expressing CD4+ T cells could be separated into 3 subsets based on their levels of intracellular FoxP3 and expression of CD45RA[10]. It is now well accepted that CD4+ T cells with low expression of FoxP3 bearing a naïve phenotype are a distinct subset of Treg cells that derive from the thymus corresponding to murine natural thymic derived Treg cells. These cells can be simply flow isolated as CD45RA+CD25+CD4+ T cells[10].

Regarding CD45RA−FoxP3 expressing cells, FoxP3$^{high}$ cells are highly suppressive while CD4+ T cells with low expression of FoxP3 do not suppress. The latter probably correspond to conventional T cells with activation induced expression of FoxP3, although not high enough to acquire a suppressive function[29, 30].

FoxP3$^{high}$ cells encompass Treg cells expressing HLA-DR and/or ICOS. Both markers have been shown to characterize subsets of Treg cells that are highly and rapidly suppressive[15] and that produce IL-10 respectively[14]. More recently, Shevach's group has proposed that transcription factor Helios was a marker for natural Treg cells[16]. However recent findings have demonstrated that CD4$^+$ T cells with induced expression of FoxP3 and other activated CD4$^+$ T cells could also express Helios[31-33].

Because it was unclear whether the FoxP3$^{high}$ effector Treg cells could be defined as a discreet population with a single specific surface marker, we decided to analyze all known surface markers for which antibodies for flow cytometry were available.

The study of more than 340 surface markers allowed us to define 18 markers highly upregulated by eTreg cells among which 6 markers (CD25, HLA-DR, CD39, CD95, CD147, and ICOS)[4, 14, 15, 17-20] have been already described. 7 other surface molecules were downregulated but none of them was better than CD127 to define FoxP3$^+$ cells.

ICOS was highly correlated with the expression of Ki-67, indicating that ICOS is rather a marker for proliferating eTreg cells than a marker for a particular population. Together with Ito's report, this result indicates that proliferating ICOS$^+$Ki-67$^+$ eTreg cells produce IL-10[14]. We failed to determine a specific surface marker for Helios except CD39 which was highly correlated with Helios in some donors but not all. This result indicates that Helios$^+$ and CD39$^+$Treg cells are probably the same subset within the eTreg cells.

We finally found that CD15s was the best candidate as a putative specific marker for eTregs as CD15s was highly expressed on FoxP3$^{high}$ cells but not on both nTreg cells and FoxP3$^{low}$CD45RA$^-$CD4$^+$ T cells. We could confirm that CD15s$^+$FoxP3$^{+(high)}$ cells were highly suppressive while CD15s$^-$FoxP3$^{+(low)}$ were not conferring to this marker a high discriminative power. We therefore describe here for the first time a marker that is highly specific for eTreg cells.

CD15s is the α2-3 sialosylated form of lacto-N-fucopentaose III (CD15), also known as sialyl Lewisx (sLEx) which is a tetrasaccharide carbohydrate[34]. The glucidic nature of this antigen explains why previous attempts to determine specific surface markers through transcriptome analysis failed to identify this molecule[10]. However, careful retrospective analysis of our previous transcriptome analysis indicated that fucosyltransferase 7 (alpha (1,3) fucosyltransferase), which is required for the synthesis of CD15s from CD15[35], was indeed specifically upregulated in the eTreg subset.

We also analyzed the expression of CD15s together with other known activation markers born by peripheral eTreg cells in Treg cells developing in the thymus. We could establish a stepwise differentiation dynamic for thymic developing Treg cells by analyzing the levels of FoxP3, Ki-67, CD45RA and CD31 in double positive and single CD4$^+$ positive FoxP3$^+$ thymocytes. We could confirm that FoxP3 expression was initiated at a DP stage at high levels together with the expression of ICOS and CD15s[14]. Both markers were not present in SP CD4$^+$ CD31$^+$FoxP3$^{low}$ cells indicating that both markers are transiently expressed in the thymus and are not present in thymus emigrating cells.

Finally, we confirmed that CD15s was a relevant marker for eTreg cells in diseases. We observed that the prevalence of eTreg cells using the definition of Treg subsets based on the expression of FoxP3, CD45RA and Ki-67 was unmodified in healthy donors and slightly overestimated in sarcoidosis[1] and slightly underestimated in SLE[2] when using CD15s as an additional marker for eTreg cells. Of note, the abnormalities observed in FoxP3 expressing CD4$^+$ T cell subsets were still present and remarkable using this marker. Finally, we applied this new definition to the PBMCs of a subject with mild untreated mycosis fungocides[27, 28] and could observe a clear distinct population of CD15s$^+$ FoxP3$^{high}$ eTreg cells.

We therefore propose that CD15s be added in any phenotypic flow analysis of FoxP3 expressing CD4$^+$ T cells subsets in human studies in addition to, at least, CD45RA and to CD25, CD127 and CD45RA for flow separation of FoxP3 expressing subsets for functional analysis.

Because CD15s is upregulated on expanding nTreg cells, we also propose CD15s as a quality control marker to assess the purity of expanding Treg cells in vitro. Indeed, using IL-2 and rapamycin, CD15s was present in only 20-30% of proliferating nTreg cells indicating that IL-2 and ramycin alone may not be optimal to obtain highly pure FoxP3$^{high}$ eTreg cells upon culture[36].

Because we flow isolated CD15s$^+$ eTreg cells using antibodies that specifically recognize CD15s and not CD15, it is highly improbable that CD15s itself participates in the in vitro and the in vivo contact dependent Treg mediated suppression[37]. However, because CD15s is a ligand for selectins and is involved in the cellular interaction with endothelial cells in order to promote the migration from peripheral blood into the tissues[38], CD15s is probably involved in the transmigration of eTreg cells in target tissues, thus participating in their suppressive function in vivo. CD15s is also highly expressed on monocytes and some myeloid precursors[39]. This may compromise the use of monoclonal antibodies aiming the neutralization of the transmigration of eTreg cells into tissues in order to promote effector immune responses. Better understanding of the molecular mechanisms of the upregulation of CD15s in eTreg may help provide new therapeutic targets in enhancing or neutralizing suppressing effects of eTreg cells.

In conclusion, we have demonstrated that CD15s was a marker for eTreg cells that confirms the relevance of the previously proposed classification for FoxP3 expressing CD4$^+$ T cell subsets. We therefore recommend the use of CD15s in addition to CD45RA for the phenotypic and functional analysis of human FoxP3 expressing CD4$^+$T cells.

REFERENCES

Throughout this application, various references describe the state of the art to which this invention pertains. The disclosures of these references are hereby incorporated by reference into the present disclosure.

1. Sakaguchi, S., Yamaguchi, T., Nomura, T. & Ono, M. Regulatory T cells and immune tolerance. *Cell* 133, 775-787 (2008).
2. Sakaguchi, S., Miyara, M., Costantino, C. M. & Hafler, D. A. FOXP3(+) regulatory T cells in the human immune system. *Nat. Rev. Immunol.* 10, 490-500 (2010).
3. Walker, M. R. et al. Induction of FoxP3 and acquisition of T regulatory activity by stimulated human CD4(+)CD25 (−) T cells. *J. Clin. Invest.* 112, 1437-1443 (2003).
4. Gavin, M. A. et al. Single-cell analysis of normal and FOXP3-mutant human T cells: FOXP3 expression without regulatory T cell development. *Proc. Natl. Acad. Sci. U.S.A.* 103, 6659-6664 (2006).

5. Allan, S. E. et al. Activation-induced FOXP3 in human T effector cells does not suppress proliferation or cytokine production. *Int. Immunol.* 19, 345-354 (2007).
6. Tran, D. Q., Ramsey, H. & Shevach, E. M. Induction of FOXP3 expression in naïve human CD4(+)FOXP3(−) T cells by T-cell receptor stimulation is transforming growth factor-beta-dependent but does not confer a regulatory phenotype. *Blood* 110, 2983-2990 (2007).
7. Wang, J., Ioan-Facsinay, A., Van der Voort, E. I. H., Huizinga, T. W. J. & Toes, R. E. M. Transient expression of FOXP3 in human activated nonregulatory CD4(+) T cells. *Eur. J. Immunol.* 37, 129-138 (2007).
8. Miyara, M. et al. Functional Delineation and Differentiation Dynamics of Human CD4(+) T Cells Expressing the FoxP3 Transcription Factor. *Immunity* 30, 899-911 (2009).
9. Valmori, D., Merlo, A., Souleimanian, N. E., Hesdorffer, C. S. & Ayyoub, M. A peripheral circulating compartment of natural naïve CD4(+) Tregs. *J. Clin. Invest.* 115, 1953-1962 (2005).
10. Fritzsching, B. et al. Naive regulatory T cells: a novel subpopulation defined by resistance toward CD95L-mediated cell death. *Blood* 108, 3371-3378 (2006).
11. Seddiki, N. et al. Persistence of naive CD45RA+ regulatory T cells in adult life. *Blood* 107, 2830-2838 (2006).
12. Ito, T. et al. Two functional subsets of FOXP3+ regulatory T cells in human thymus and periphery. *Immunity* 28, 870-880 (2008).
13. Baecher-Allan, C., Wolf, E. & Hafler, D. A. MHC class II expression identifies functionally distinct human regulatory T cells. *J Immunol* 176, 4622-4631 (2006).
14. Thornton, A. M. et al. Expression of Helios, an Ikaros transcription factor family member, differentiates thymic-derived from peripherally induced Foxp3+T regulatory cells. *J Immunol* 184, 3433-3441 (2010).
15. Borsellino, G. et al. Expression of ectonucleotidase CD39 by Foxp3+Treg cells: hydrolysis of extracellular ATP and immune suppression. *Blood* 110, 1225-1232 (2007).
16. Deaglio, S. et al. Adenosine generation catalyzed by CD39 and CD73 expressed on regulatory T cells mediates immune suppression. *The Journal of experimental medicine* 204, 1257-1265 (2007).
17. Fritzsching, B. et al. In contrast to effector T cells, CD4+CD25+FoxP3+ regulatory T cells are highly susceptible to CD95 ligand—but not to TCR-mediated cell death. *J Immunol* 175, 32-36 (2005).
18. Solstad, T. et al. CD147 (Basigin/Emmprin) identifies FoxP3+CD45RO+CTLA4+-activated human regulatory T cells. *Blood* 118, 5141-5151 (2011).
19. Liu, W. H. et al. CD127 expression inversely correlates with FoxP3 and suppressive function of human CD4(+) T reg cells. *J. Exp. Med.* 203, 1701-1711 (2006).
20. Seddiki, N. et al. Expression of interleukin (IL)-2 and IL-7 receptors discriminates between human regulatory and activated T cells. *J. Exp. Med.* 203, 1693-1700 (2006).
21. Hoffmann, P. et al. Only the CD45RA(+) subpopulation of CD4(+)CD25(high) T cells gives rise to homogeneous regulatory T-cell lines upon in vitro expansion. *Blood* 108, 4260-4267 (2006).
22. Battaglia, M. et al. Rapamycin promotes expansion of functional CD4(+)CD25(+)FOXP3(+) regulatory T cells of both healthy subjects and type 1 diabetic subjects. *J. Immunol.* 177, 8338-8347 (2006).
23. Nunes-Cabaco, H., Caramalho, I., Sepulveda, N. & Sousa, A. E. Differentiation of human thymic regulatory T cells at the double positive stage. *European journal of immunology* 41, 3604-3614 (2011).
24. Miyara, M., Amoura, Z. & Gorochov, G. Human lupus, fewer Treg cells indeed: comment on the article by Venigalla et al. *Arthritis and rheumatism* 60, 630 (2009).
25. Miyara, M. et al. Global natural regulatory T cell depletion in active systemic lupus erythematosus. *J. Immunol.* 175, 8392-8400 (2005).
26. Hallermann, C., Niermann, C. & Schulze, H. J. Regulatory T-cell phenotype in association with large cell transformation of mycosis fungoides. *European journal of haematology* 78, 260-263 (2007).
27. Krejsgaard, T., Odum, N., Geisler, C., Wasik, M. A. & Woetmann, A. Regulatory T cells and immunodeficiency in mycosis fungoides and Sezary syndrome. *Leukemia* 26, 424-432 (2012).
28. Wan, Y. Y. & Flavell, R. A. Regulatory T-cell functions are subverted and converted owing to attenuated Foxp3 expression. *Nature* 445, 766-770 (2007).
29. Allan, S. E., Song-Zhao, G. X., Abraham, T., McMurchy, A. N. & Levings, M. K. Inducible reprogramming of human T cells into Treg cells by a conditionally active form of FOXP3. *Eur J Immunol* 38, 3282-3289 (2008).
30. Gottschalk, R. A., Corse, E. & Allison, J. P. Expression of Helios in peripherally induced Foxp3+ regulatory T cells. *J Immunol* 188, 976-980 (2012).
31. Himmel, M. E., MacDonald, K. G., Garcia, R. V., Steiner, T. S. & Levings, M. K. Helios+ and Helios− cells coexist within the natural FOXP3+ T regulatory cell subset in humans. *J Immunol* 190, 2001-2008 (2013).
32. Serre, K. et al. Helios is associated with CD4 T cells differentiating to T helper 2 and follicular helper T cells in vivo independently of Foxp3 expression. *PloS one* 6, e20731 (2011).
33. Munro, J. M. et al. Expression of sialyl-Lewis X, an E-selectin ligand, in inflammation, immune processes, and lymphoid tissues. *The American journal of pathology* 141, 1397-1408 (1992).
34. Rabina, J., Smithers, N., Britten, C. J. & Renkonen, R. A time-resolved immunofluorometric method for the measurement of sialyl Lewis x-synthesizing alpha1,3-fucosyltransferase activity. *Analytical biochemistry* 246, 71-78 (1997).
35. Miyara, M. et al. The immune paradox of sarcoidosis and regulatory T cells. *The Journal of experimental medicine* 203, 359-370 (2006).
36. Miyara, M., Wing, K. & Sakaguchi, S. Therapeutic approaches to allergy and autoimmunity based on FoxP3+ regulatory T-cell activation and expansion. *The Journal of allergy and clinical immunology* 123, 749-755; quiz 756-747 (2009).
37. Miyara, M. & Sakaguchi, S. Natural regulatory T cells: mechanisms of suppression. *Trends in molecular medicine* 13, 108-116 (2007).
38. Polley, M. J. et al. CD62 and endothelial cell-leukocyte adhesion molecule 1 (ELAM-1) recognize the same carbohydrate ligand, sialyl-Lewis x. *Proc Natl Acad Sci USA* 88, 6224-6228 (1991).
39. Easton, E. W., Schiphorst, W. E., van Drunen, E., van der Schoot, C. E. & van den Eijnden, D. H. Human myeloid alpha 3-fucosyltransferase is involved in the expression of the sialyl-Lewis(x) determinant, a ligand for E- and P-selectin. *Blood* 81, 2978-2986 (1993).

The invention claimed is:

1. A method for identifying effector Treg (eTreg) cells in a sample comprising the steps of i) identifying a population of Treg cells;
ii) detecting cell surface expression of CD15s in the population of Treg cells; and
iii) concluding that Treg cells expressing CD15s are the eTreg cells.

2. The method of claim 1, wherein the sample is a fluid sample, and wherein the method of identifying a population of Treg cells comprises
iv) detecting cell surface expression of CD127, CD4 and CD25 in the population of Treg cells; and
v) concluding that cells expressing CD127 at low levels, and expressing CD4 and CD25, are the Treg cells.

3. The method according to claim 2 wherein the fluid sample is selected from the group consisting of blood samples, peripheral blood mononuclear cells (PBMC) samples and samples of Treg cells in suspension.

4. The method of claim 2 wherein the step of detecting is performed with a set of antibodies specific for CD4, CD25 and CD127.

5. The method of claim 2 wherein the step of detecting comprises performing flow cytometry.

6. The method of claim 2 which further comprises a step of detecting cell surface expression of CD45RA.

7. The method of claim 2 which further comprises a step of determining the level of eTreg cells present in the sample.

8. The method of claim 2 which further comprises a step of isolating eTreg cells from the sample.

* * * * *